United States Patent
Berthier et al.

(10) Patent No.: US 10,426,390 B2
(45) Date of Patent: Oct. 1, 2019

(54) DEVICES, SYSTEMS AND METHODS FOR ACTUATION AND RETRACTION IN FLUID COLLECTION

(71) Applicant: Tasso, Inc., Seattle, WA (US)

(72) Inventors: Erwin Berthier, Seattle, WA (US); Ben Casavant, Seattle, WA (US); Ben Moga, Soquel, CA (US)

(73) Assignee: Tasso, Inc., Seattle, WA (US)

( * ) Notice: Subject to any disclaimer, the term of this patent is extended or adjusted under 35 U.S.C. 154(b) by 209 days.

(21) Appl. No.: 15/387,177

(22) Filed: Dec. 21, 2016

(65) Prior Publication Data

US 2017/0172481 A1    Jun. 22, 2017

Related U.S. Application Data

(60) Provisional application No. 62/270,550, filed on Dec. 21, 2015.

(51) Int. Cl.
*A61B 5/151* (2006.01)
*A61B 5/15* (2006.01)

(52) U.S. Cl.
CPC .... *A61B 5/15115* (2013.01); *A61B 5/150022* (2013.01); *A61B 5/150099* (2013.01); *A61B 5/15113* (2013.01); *A61B 5/15117* (2013.01); *A61B 5/15144* (2013.01); *A61B 5/150167* (2013.01); *A61B 5/150175* (2013.01); *A61B 5/150221* (2013.01); *A61B 5/150236* (2013.01); *A61B 5/150916* (2013.01); *A61B 5/150984* (2013.01)

(58) Field of Classification Search
CPC ............ A61B 5/15115; A61B 5/15144; A61B 5/15117; A61B 5/15113; A61B 5/150977; A61B 5/150984; A61B 5/150916; A61B 5/150167; A61B 5/150022; A61B 5/150175; A61B 5/150236; A61B 5/150221; A61B 5/150053; A61B 5/150099; A61B 5/150068
See application file for complete search history.

(56) References Cited

U.S. PATENT DOCUMENTS

| 4,677,979 | A | * | 7/1987 | Burns | A61B 5/15113 606/172 |
| 4,775,366 | A | | 10/1988 | Rosenblatt | |
| 5,395,387 | A | * | 3/1995 | Burns | A61B 5/150022 606/181 |
| 6,419,661 | B1 | | 7/2002 | Kuhr et al. | |
| 6,659,975 | B2 | | 12/2003 | Amano et al. | |
| 7,238,192 | B2 | * | 7/2007 | List | A61B 5/150022 606/167 |
| 8,361,099 | B2 | * | 1/2013 | Schosnig | A61B 5/150022 606/167 |
| 2006/0052809 | A1 | | 3/2006 | Karbowniczek et al. | |
| 2007/0010841 | A1 | | 1/2007 | Teo et al. | |
| 2010/0145377 | A1 | | 6/2010 | Lai et al. | |

* cited by examiner

*Primary Examiner* — David J. McCrosky
(74) *Attorney, Agent, or Firm* — Perkins Coie LLP

(57) ABSTRACT

The disclosed apparatus, systems and methods relate to devices, systems and methods for the collection of bodily fluids involving a single-use actuation and retraction mechanism disposed within a collector.

11 Claims, 21 Drawing Sheets

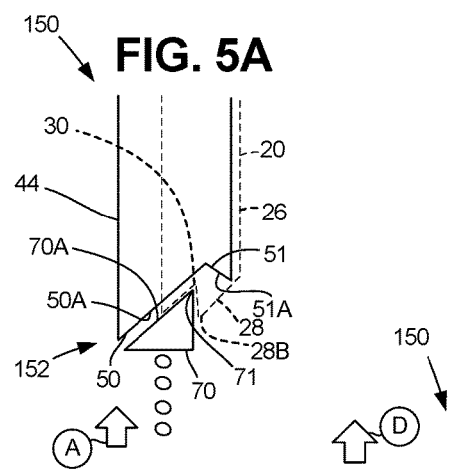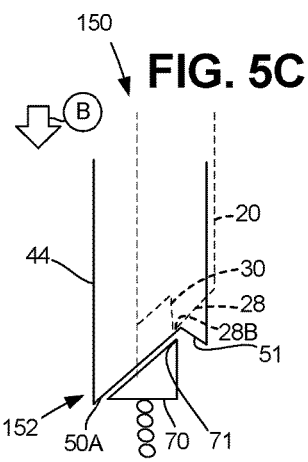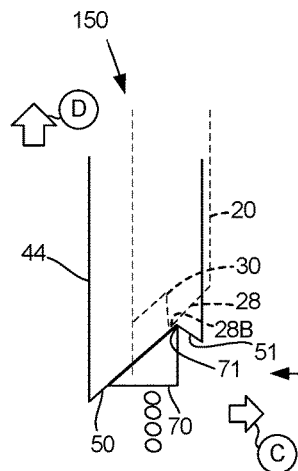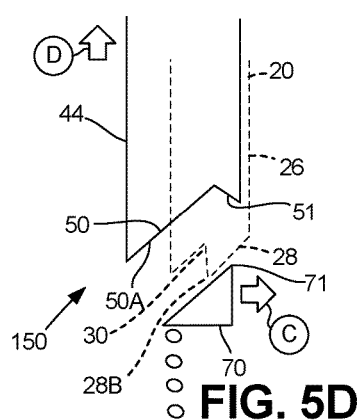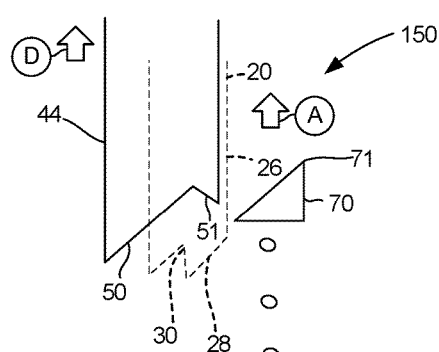

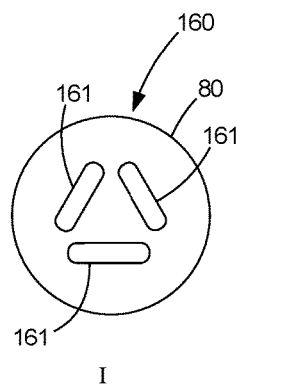 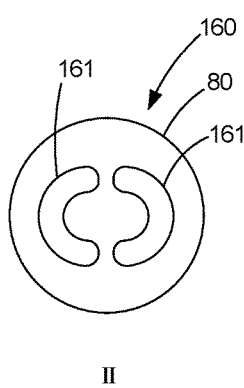 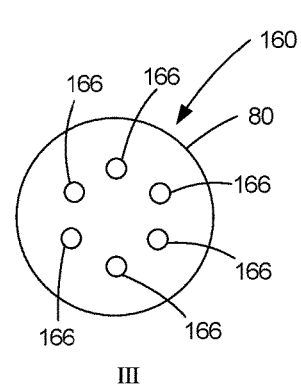
I
FIG. 11A
II
FIG. 11B
III
FIG. 11C
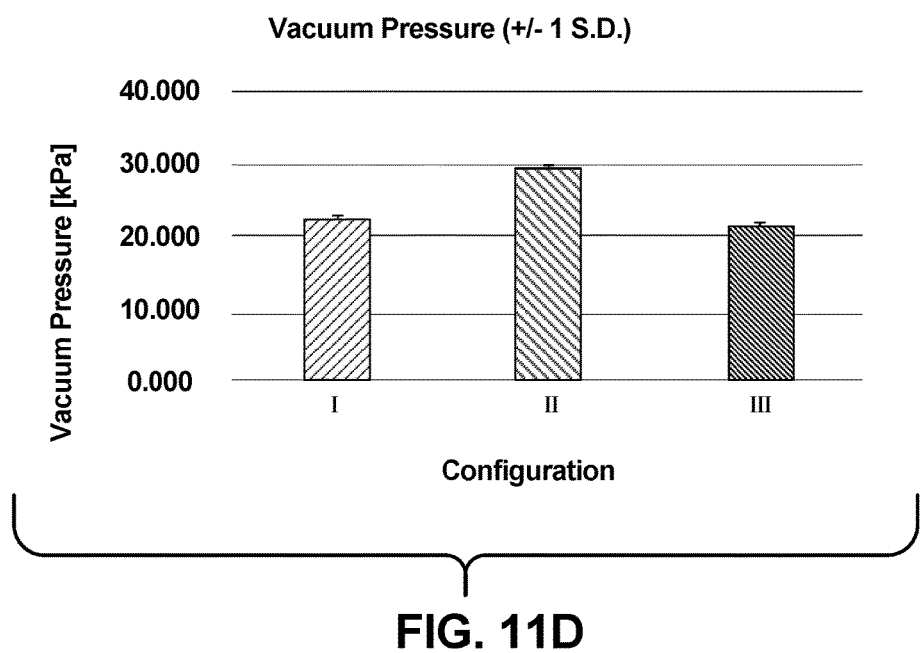
FIG. 11D

DEVICES, SYSTEMS AND METHODS FOR ACTUATION AND RETRACTION IN FLUID COLLECTION

CROSS-REFERENCE TO RELATED APPLICATIONS

This application claims priority to U.S. Provisional Patent Application Ser. No. 62/270,550, filed Dec. 21, 2015 and entitled "Devices, Systems And Methods For Actuation And Retraction In Fluid Collection," which is hereby incorporated herein by reference in its entirety.

FEDERALLY SPONSORED RESEARCH OR DEVELOPMENT

This invention was made with government support under Contract # W31P4Q14C0006 awarded by DARPA. The government has certain rights in the invention.

TECHNICAL FIELD

The disclosed technology relates generally to the collection of bodily fluids, and in particular, to the devices, systems, and methods providing for the collection of bodily fluids into a receptacle and, in certain embodiments, utilizing force and energy minimums on the fluid being collected to add functionality by way of a guidance mechanism for full lancet penetration, safe lancet storage and vacuum creation. These embodiments have implications for active fluid collection, safety and manufacturing.

BACKGROUND

Devices, systems and methods to collect bodily fluids are necessary devices for the growing field of personalized medicine. As point-of-care devices continue to improve, an often overlooked area lies within the collection of samples from untrained users. Currently, biological samples are most commonly obtained via either simple-to-use methods or devices, as with generic lancing devices, or trained personnel, as with phlebotomy venipunctures. In order to transfer the bodily fluid to a container, receptacle, or an analysis device, multiple steps are required that are time consuming, error prone and/or cumbersome.

Thus, there is a need in the art for improved microfluidic devices for fluid handling and transfer, and related systems and methods.

BRIEF SUMMARY

Discussed herein are various embodiments of the collection device, as well as associated systems and methods for its use. For brevity, these embodiments may be described in relation to a "collector," though that is not intended to limit the scope of the disclosure in any way.

In one Example a collector is provided including a housing including proximal and distal ends and a lumen, an actuator disposed within the lumen, a platform disposed within the lumen and distal to the actuator, single use actuation mechanism in operational communication with the platform, and a plunger including at least one lancet, wherein the single actuation mechanism is configured to translate linear force applied to the actuator into rotational force on the platform and urge the plunger distally.

Implementations of this Example may include one or more of the following features. The collector further including a membrane disposed within the lumen, where the membrane is configured to create a fluidic seal within the lumen. The collector where the membrane includes a membrane lumen and a one way valve configured to create a vacuum within the membrane lumen. The collector where the membrane includes a bellows. The collector where plunger is configured to retract after actuation. The collector where the platform includes at least one projection which is in operational communication with the single actuation mechanism. The collector where the single actuation mechanism includes at least one actuator arm and at least one elongate guide. The collector where the single actuation mechanism is configured so as rotate the platform during actuation by way of the projection. The collector where the housing includes at least one elongate guide including a guide groove. The collector further including a spring configured urge the at least one projection into the guide groove. The collector where the at least one actuator arm is configured to urge the projection distally and dislodge it from the guide groove in response to actuation. The collector further including a variable width guide face. The collector where the at least one projection includes a projection face configured to rotate the platform when the projection is urged distally.

In another Example, a single use fluid collector is provided, including: a housing including proximal and distal ends and a lumen, an actuator including at least one actuator arm disposed within the lumen, and a platform including at least one projection disposed within the lumen and distal to the actuator. The single use fluid collector also includes where the at least one actuator arm is in translational and rotational communication with the platform via the at least one projection.

Implementations of this Example may include one or more of the following features. The collector where the housing includes at least one elongate guide including a guide groove. The collector further including a spring configured urge the at least one projection into the guide groove. The collector where the at least one actuator arm is configured to urge the projection distally and dislodge it from the guide groove in response to actuation. The collector further including a variable width guide face. The collector where the at least one projection includes a projection face configured to rotate the platform when the projection is urged distally. The system where at least one actuator arm is in operational communication with the at least one projection to translate linear force from the arm into rotational force on the platform. The system where at least one elongate guide includes a guide notch. The system where at least one actuator arm includes an actuator catch. The system further including an actuation mechanism configured to increase platform residence time. The system further including a membrane collar.

In another Example, an actuation and retraction system for use in a medical device is provided, the system including: a housing including a central lumen extending through the housing and including at least one elongate guide disposed within the central lumen, an actuator including at least one actuator arm extending distally adjacent to the at least one elongate guide, a platform disposed within the lumen, the platform including at least one projection, and a plunger.

Implementations of this Example may include one or more of the following features. The system where at least one actuator arm is in operational communication with the at least one projection to translate linear force from the arm into rotational force on the platform. The system where at least one elongate guide includes a guide notch. The system where at least one actuator arm includes an actuator catch. The system further including an actuation mechanism configured to increase platform residence time. The system further including a membrane collar.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 5A is a side view of another embodiment of an actuation mechanism.

FIG. 5B is a side view of the actuation mechanism embodiment of FIG. 5A, during rotation.

FIG. 5C is a side view of the actuation mechanism embodiment of FIG. 5A, during rotation.

FIG. 5D is a side view of the actuation mechanism embodiment of FIG. 5A, during rotation.

FIG. 5E is a side view of the actuation mechanism embodiment of FIG. 5A, during retraction.

FIG. 11A is a top schematic view of a membrane one embodiment of the one-way valve.

FIG. 11B is a top schematic view of a membrane another embodiment of the one-way valve.

FIG. 11C is a top schematic view of a membrane another embodiment of the one-way valve.

FIG. 11D is a histogram showing the vacuum pressure generated by the embodiments of FIGS. 11A-C.

DETAILED DESCRIPTION

The various embodiments disclosed or contemplated herein relate to a single device that can be used by untrained or minimally-trained persons to both collect bodily fluid and seamlessly contain the bodily fluid, and related systems and methods. These devices, systems and methods generally relate to a collector for bodily fluids having an actuator—or "button"—at one end and at least one lancet disposed within the opposite end. In these implementations, when the button is depressed, an actuation mechanism is deployed—the lancets extend to pierce the skin of a subject for the collection of fluid, and the actuator is disabled from further use. Further description of the structure and function of these embodiments is found herein.

It is understood that the various embodiments of devices, methods and systems disclosed herein can be incorporated into or used with any other known medical devices, systems, and methods. For example, the various embodiments disclosed herein may be incorporated into or used with any of the medical devices and systems disclosed in co-pending U.S. Pat. No. 9,289,763, filed Jul. 23, 2013, entitled "Methods, Systems, and Devices Relating to Open Microfluidic Channels," U.S. application Ser. No. 14/932,485, filed Nov. 4, 2015, entitled "Methods, Systems, and Devices Relating to Open Microfluidic Channels," U.S. application Ser. No. 13/750,526, filed Jan. 25, 2013, entitled "Handheld Device for Drawing, Collecting, and Analyzing Bodily Fluid," and U.S. application Ser. No. 14/816,994, filed Aug. 3, 2015, entitled Devices, Systems and Methods for Gravity-Enhanced Microfluidic Collection, Handling and Transferring of Fluids," all of which are hereby incorporated herein by reference in their entireties.

Figure 1A:
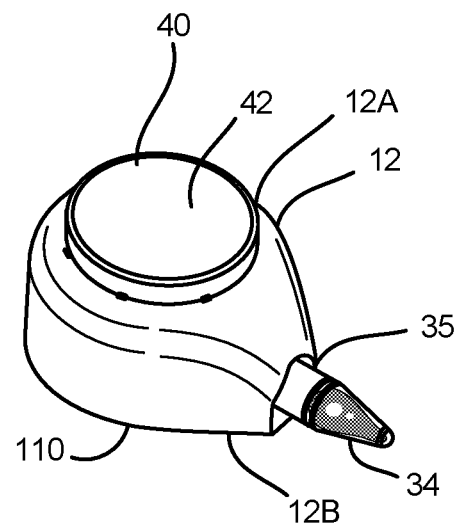
FIG. 1A is a perspective external view of the collector, according to one embodiment.
Figure 1B:
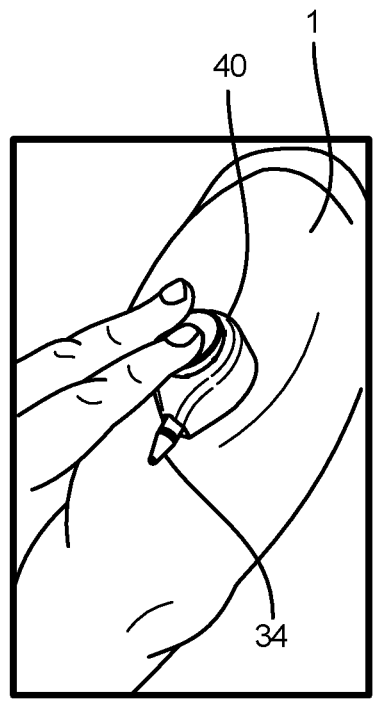
FIG. 1B is a perspective view of the collector of FIG. 1A placed on the skin of a subject.

Turning to the figures with greater detail, FIGS. 1A-1B depict exemplary embodiments of the gravity-enhanced fluid collection device, or simply "collector" 10. As is shown in FIGS. 1A-B, in exemplary embodiments, the collector 10 generally comprises a housing 12 having proximal 12A and distal 12B ends with an actuator 40 disposed there through, having a push button 42.

In use, the collector 10 provides for both the actuation and retraction of the collector's 10 internal components with a single application of force to the actuator 40, or "button," which passes into the collector housing 12 and comes to a rest. In exemplary embodiments, the collector 10 is used to facilitate the puncture of the skin of a subject 1 for collection of fluid in the reservoir 34 by way of a fitting or coupling portion 35, which is also called a "collar" in certain embodiments.

In exemplary embodiments, the reservoir 34 can be removably attached to the housing 12, by way of the coupling portion 35, such that it may be detached, as has been previously described in the incorporated references. In certain embodiments, the reservoir 34 can be a standard Eppendorf tube press-fitted on the fitting 35. In further embodiments, the reservoir 34 can also be custom made and utilize capillary forces or solely gravitational forces to fill, as has also been previously described, such as in U.S. application Ser. No. 14/816,994, which has been incorporated herein by reference. The tube 34 can thus act as a removable and standardized reservoir 34 for containing or gathering the fluid that can be simply and easily detached and inserted into existing and established testing or lab equipment. By way of example, where the fluid is blood, the tube 34 can be easily inserted into clinical and laboratory equipment or workflows for diagnostics and/or biomarker detections.

Figure 2A:
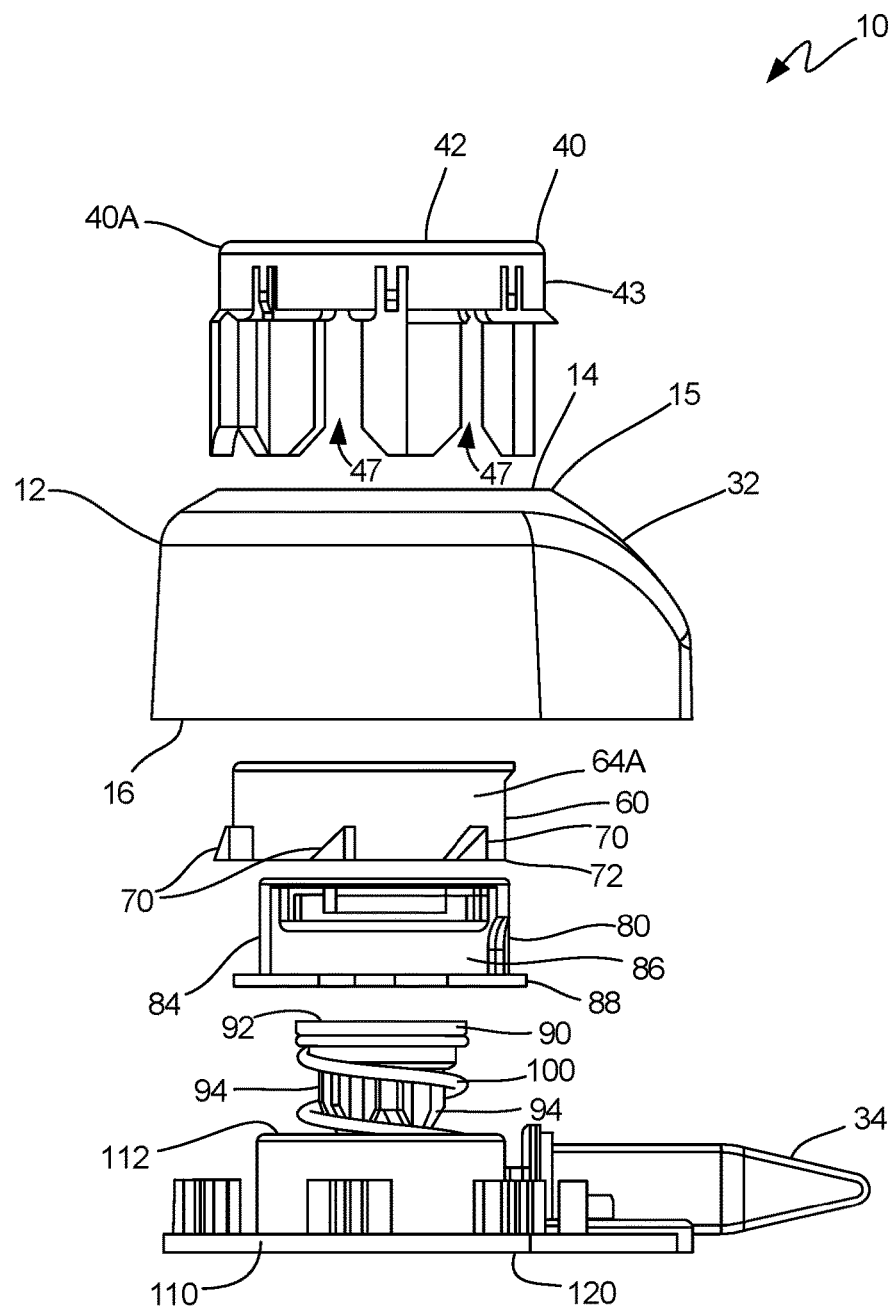
FIG. 2A is an exploded side view of an exemplary embodiment of the collector.
Figure 2B:
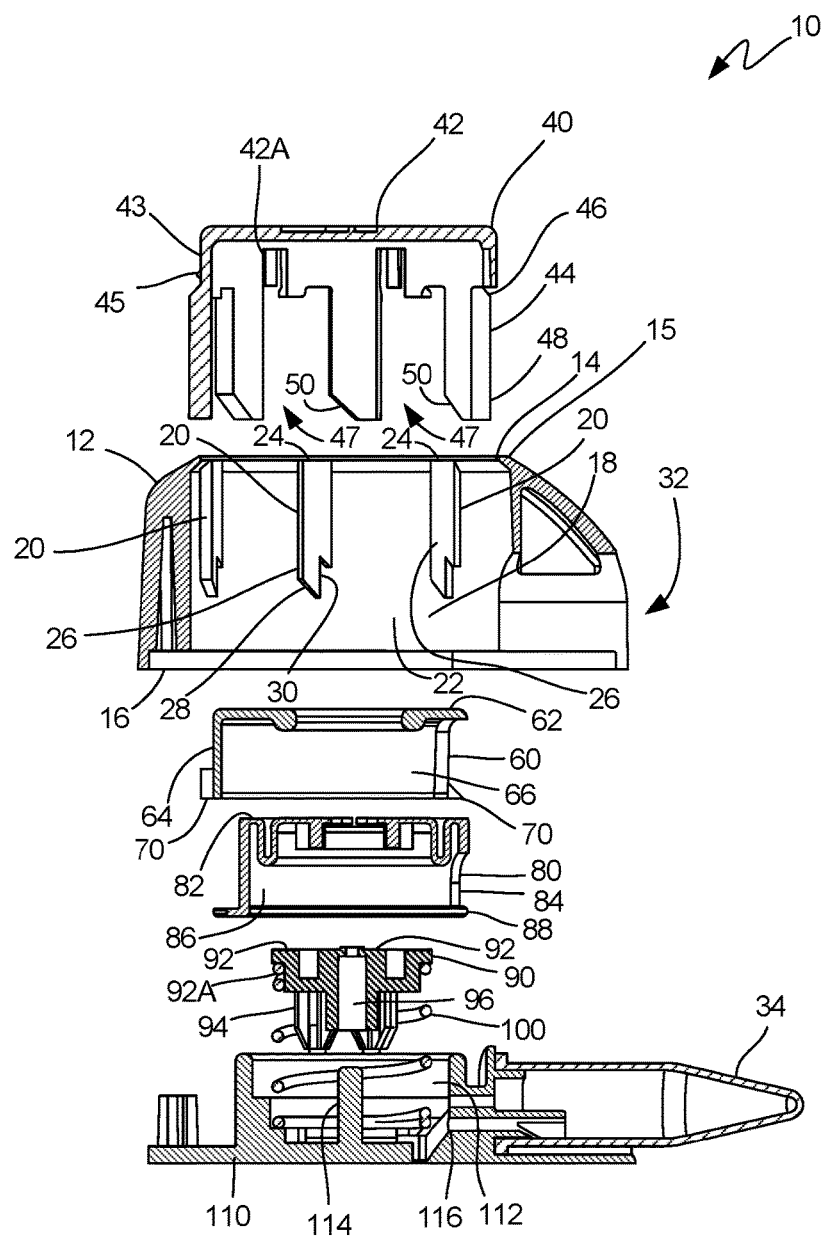
FIG. 2B is a cross-sectional view of the embodiment of FIG. 2A.
Figure 2C:
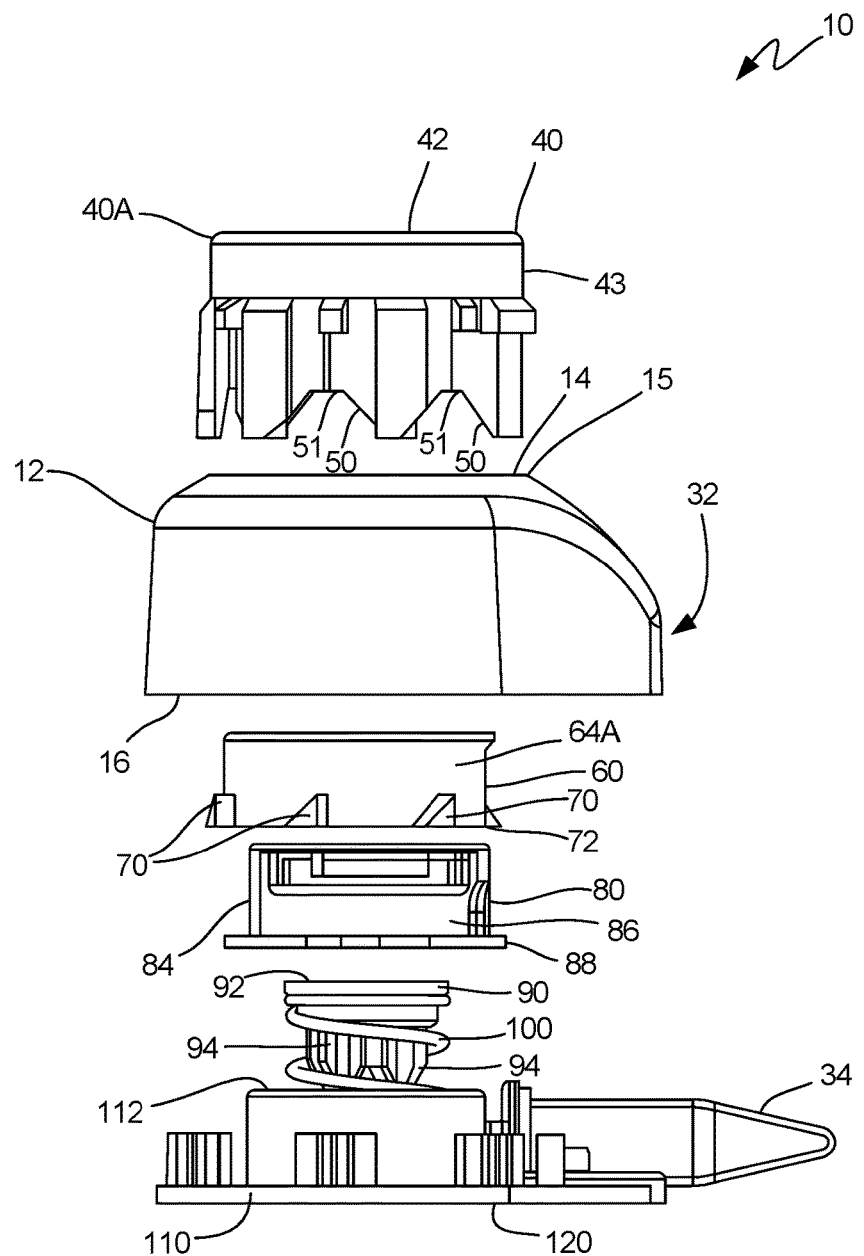
FIG. 2C is an exploded side view of the collector according to an alternative embodiment.
Figure 2D:
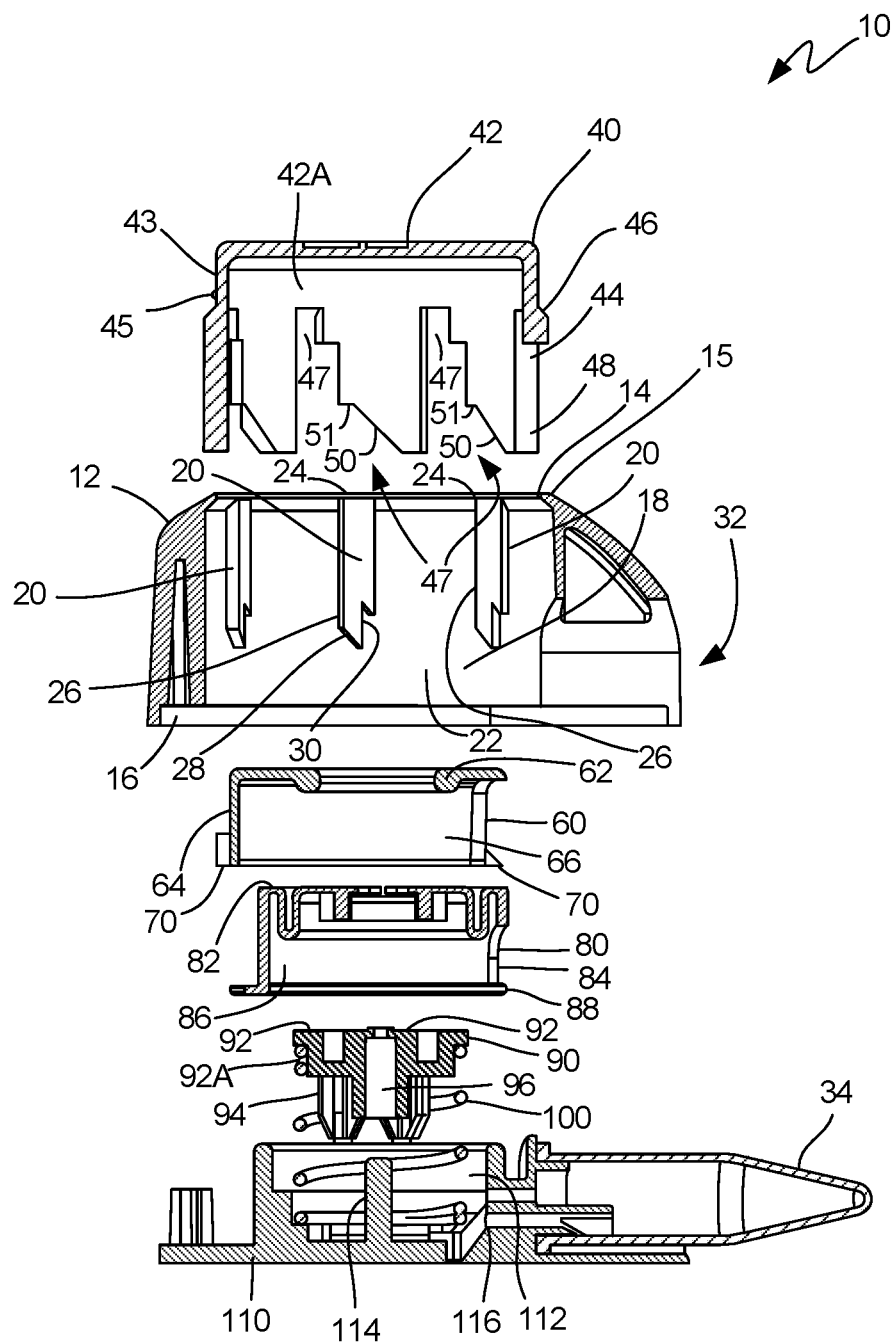
FIG. 2D is a cross-sectional view of the embodiment of FIG. 2C.
Figure 3A:
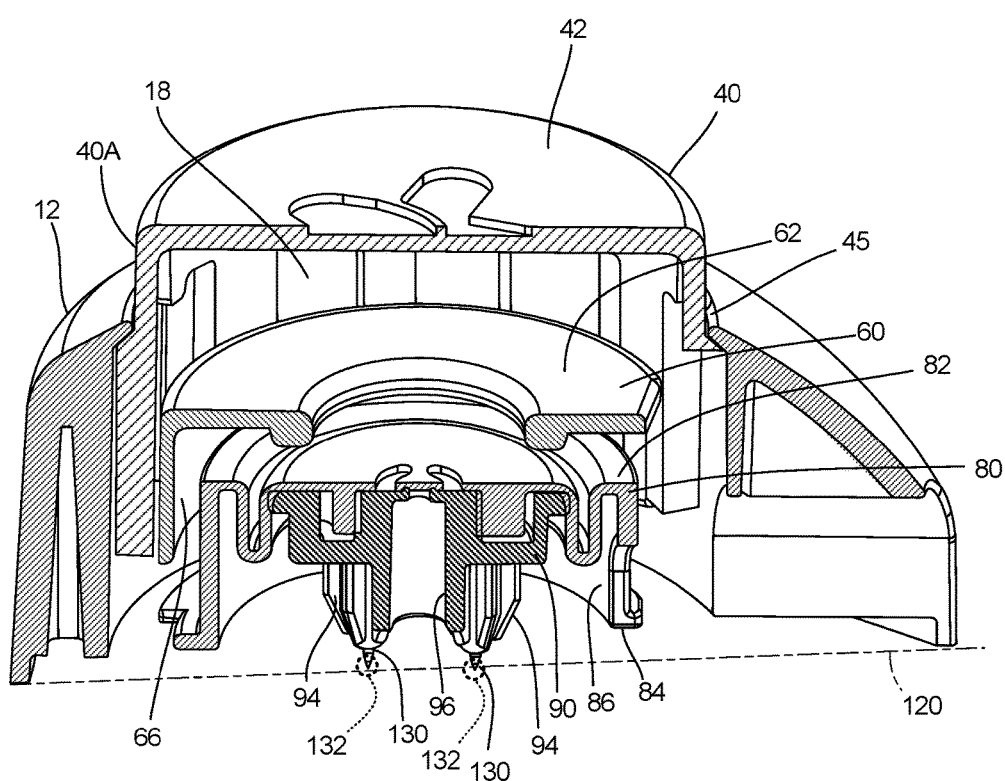
FIG. 3A is a perspective cross-sectional view of the internal components of the collector, according to one embodiment.
Figure 3B:
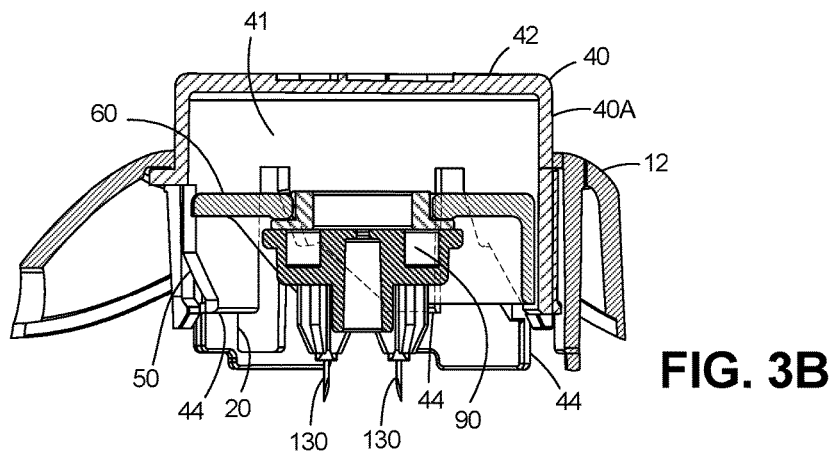
FIG. 3B is a cross-sectional view of the internal components, before actuation, according to the embodiment of FIG. 3A
Figure 3C:
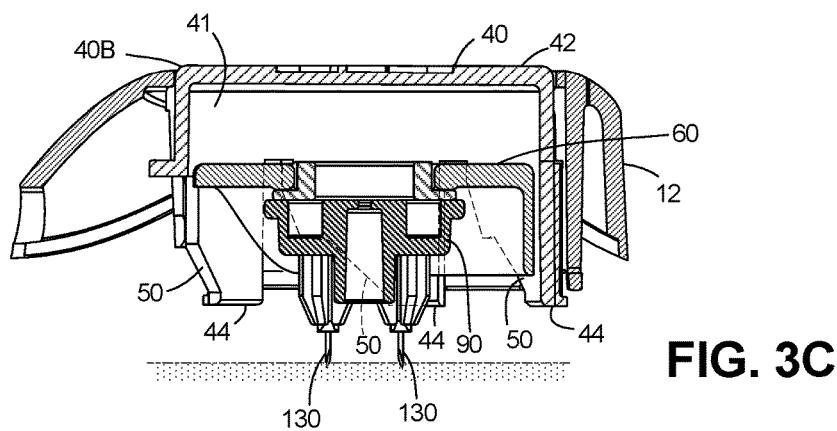
FIG. 3C is a cross-sectional view of the internal components, during actuation, according to the embodiment of FIG. 3A

An exemplary embodiment of a collector 10 that can be used to both collect bodily fluid and contain the fluid is shown in FIGS. 2A-3C. FIGS. 2A-2D depict the internal components of the collector 10, according to various embodiments. FIGS. 3A-3C depict the various internal components of the collector 10 in use.

As shown generally in FIGS. 2A-2D, in these embodiments, the collector 10 comprises a housing 12 that has an actuator 40, a platform 60, a membrane 80, a plunger 90 and a base 110. In exemplary embodiments, these components are disposed in operational communication through a central lumen 18 of the housing 12 (as best shown in FIGS. 2B, 2D and 3A), so as to facilitate the puncture of the skin of a subject at the distal surface 120 of the base 110 for collection by way of lancets 130 (as best shown in FIG. 3A), as is described herein. In use, the collector 10 provides for both the actuation and retraction of the collector's internal components with a single application of force to the actuator 40, or "button," which passes into the collector body 12 and comes to a rest.

As shown in FIGS. 3A-C, the retraction phase extends the components—such as the platform 60—proximally into the actuator 40 (shown in FIG. 3C), so as not to force the button 42 upwards. The retraction also results in the creation of a vacuum within the membrane 80 so as to facilitate fluid draw, as is described further in relation to FIGS. 10A-10C. As shown in FIGS. 4A-6D, in exemplary embodiments, the combined actuation and retraction is achieved by way of a translational movement of the internal components over a prescribed distance, as will be described in further detail below. Further, in exemplary embodiments, upon retraction a vacuum can be created within a sealed portion of the actuator.

Turning to the drawings in greater detail, in the implementations of FIGS. 2A-3C, the collector 10 has a generally cylindrical housing 12 with a proximal end 14 and a distal end 16. A generally cylindrical central lumen 18 is defined within the housing 12 between the proximal end 14 and a distal end 16, as best shown in FIGS. 2B and 2D. An actuator 40 is disposed within the lumen 18, so as to be in operational communication with a platform 60, as is described in further detail in relation to FIGS. 4A-6D.

In these embodiments, as best shown in FIGS. 2A-2D, the actuator 40 has a generally planar top button surface 42 and button wall 43, so as to form the "button" 42 which protrudes (shown at 40A) above the proximal end 14 of the housing while in the "ready" position as best shown in FIG. 3 (and as discussed below in relation to FIGS. 4A-4E, FIG. 10A and FIGS. 14A-14C). The button wall 43 is substantially enclosed by a lumen lip 15 (as best shown in FIGS. 2A, 2B and 3A), which is disposed around the central lumen 18 at the proximal end 14 of the housing 12. Certain embodiments also feature a projection or threshold stop 45 as shown in FIGS. 2B and 2D. These components of the actuator 40 and housing 12 are discussed further in relation to FIGS. 8A-8C.

Continuing with the implementations of FIGS. 2A-D, the central lumen 18 has a plurality of elongate guides 20 disposed substantially from the proximal end 14 along the inner lumen surface 22. The elongate guides 20 (as best shown in FIGS. 2B and 2D) depicted have a first guide end 24 and a second guide end 26. In exemplary embodiments, the second guide end 26 further comprises a guide notch 28 and guide groove 30, the function of which are discussed below in relation to FIGS. 4A-4E. The housing 12 further comprises an outlet channel 32, which is configured to couple with a collection tube 34 when assembled, as has been previously described, for example in relation to U.S. application Ser. No. 14/816,994, which has been incorporated by reference.

In certain implementations, the actuator 40 can also have a plurality of actuator arms 44 (shown in FIGS. 2B and 2D) further comprising a first arm end 46 and second arm end 48—an arm opening 47 can be provided between the arms 46, 48 in certain implementations, as is shown in FIG. 2A, FIG. 2B and FIG. 2D.

In various implementations, the actuator arms 44 extend distally from the underside 42A of the top button surface 42, and the second arm end 48 further comprises an actuator notch 50 in these embodiments. The actuator notch 50 is discussed further below in relation to FIGS. 4A-4E and 5A-5E. In the embodiments of FIGS. 2B and 2D, the elongate guides 20 of the housing 12 can be disposed adjacent to the actuator arms 44 of the button 40 (as discussed in relation to FIGS. 4A-E), or to the interior of the lumen 18 relative to the actuator arms 44 (as is shown in FIG. 2D and discussed in relation to FIGS. 5A-5E), so as to be set "inside" the arms 44.

In the embodiments of FIGS. 2C-2D, an actuator catch 51 may also be disposed at one end of the actuator notch 50. In these implementations, the actuator catch 51 can introduce a momentary delay in the actuation and retraction process that is desirable in certain implementations. The various relationships of the elongate guides 20 to the actuator arms 44 within the lumen 18 are described further in relation to FIGS. 4A-6D and 8A-8D.

In various embodiments as best shown in FIGS. 2A-2D, the platform 60 further comprises a top platform surface 62 and a generally cylindrical platform wall 64 disposed around a platform lumen 66. In these embodiments, the platform wall 64 further comprises a plurality of platform projections 70 disposed radially about the outer wall surface 64A. In exemplary embodiments, these platform projections 70 are shaped in a manner which is complementary to the guide notch 28 and guide groove 30 of the housing 12, and actuator notch 50 of the button 40, as described in further detail below in relation to FIGS. 4A-6D. In exemplary embodiments as shown in FIGS. 2A-D, the platform projections 70 are disposed substantially at the distal wall end 72 of the platform 60, though in alternative embodiments they can be disposed near the top platform surface 62.

Turning to FIG. 3A, the platform 60 is configured to be disposed within the central lumen 18 when the collector 10 is assembled. The membrane 80 is configured to be disposed within the platform lumen 66 when the collector 10 is assembled, as best shown in FIG. 3A. The membrane 80 according to certain implementations has a top membrane surface 82 and a generally cylindrical membrane wall 84 disposed around a membrane lumen 86. As shown in FIGS. 2A-2D, in exemplary embodiments, the membrane 80 further comprises a substantially circular membrane lip 88 which is disposed on the distal end of the membrane wall 84. In exemplary embodiments, the membrane 80 and membrane lip 88 serve to create a hermetic and/or fluidic seal between a subject's skin (not shown) and the membrane lumen 86, as is discussed below in relation to FIGS. 9A-9C and FIGS. 10A-10C.

In the implementation of FIGS. 2A-3D, the plunger 90 is configured to be disposed within the membrane lumen 86 when assembled, so as to be in operational communication with the actuator 40, platform 60 and membrane 80, as will be described in further detail below in relation to FIGS. 4A-4E. In these embodiments, the plunger 90 and a spring 100 are configured to be housed within the base 110 in a generally cylindrical base lumen 112. It is understood that in use, the base 110 is configured to be disposed on underlying subject skin so as to create tension in the skin, thereby enhancing the ability to draw fluid through the collector 10 and into the collection tube 34.

Continuing with the implementations of FIGS. 2A-3D, the plunger 90 has a top plunger surface 92 and a plurality of plunger bodies 94 which extend distally from the underside 92A of the top plunger surface 92. In exemplary embodiments, the plunger 90 has a plunger coupling lumen 96 which is configured to mate with the base 110 on a base post 114. In alternative embodiments, the plunger 90 can be aligned and guided by the membrane 80. In exemplary embodiments, the spring 100 is disposed about the plunger 90 and within the base lumen 112 of the base 110 so as to be capable of urging the plunger 90 proximally.

When assembled, and as shown in FIGS. 3A-3D, the actuator 40 and platform 60 are in operational communication so as to facilitate the downward movement of the plunger 90, and accordingly the extension of the lancets 130 (shown in FIG. 3A) past the distal surface 120 (best shown in FIGS. 1A-B) and into the subject's skin (not shown). In various embodiments, and as shown in FIGS. 2A-B, the base 110 further comprises one or more fluid collection passages, sometimes called a fluidic "network" 116.

In these implementations, the network or passages 116 are in fluidic communication with the base lumen 112, apertures 132 and collection tube 34 so as to facilitate the movement of fluids from the collection apertures 132 (as shown in FIG. 3A) to the collection tube 34, such as by way of open microfluidic channels, including those capable of promoting spontaneous capillary flow in U.S. application Ser. No. 13/949,108 and the other teachings of the incorporated references above. It is understood that in various implementations the collection apertures 132 are disposed within the base lumen 112 on the distal surface 120 of the base 110.

FIGS. 3A-3DB show the assembled collector with the actuator 40 and internal components in the "ready" position, meaning that the collector 10 has not yet been actuated to collect any fluids, and the actuator 40 is disposed in an "up" position in the lumen 15, adjacent to the proximal end 14 of the housing 12. As is further discussed below in relation to FIGS. 8A-8C, the threshold stop 45 can function to prevent the movement of the actuator from the ready position absent the application of sufficient downward force from the user.

Figure 3D:
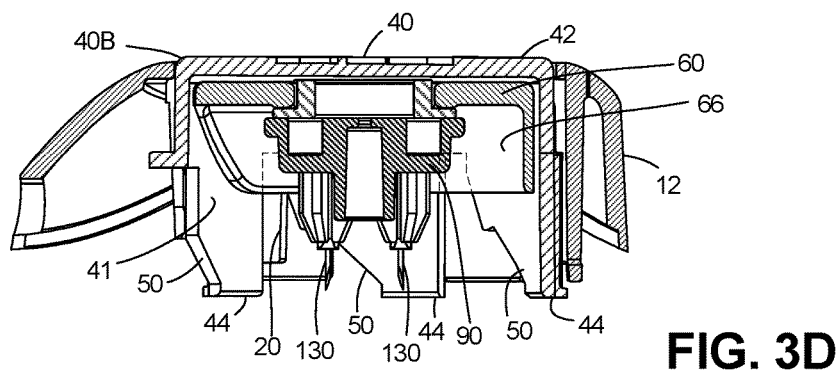
FIG. 3D is a cross-sectional view of the internal components, after retraction, according to the embodiment of FIG. 3A.

FIG. 3C-D depicts the collector 10 after actuation and retraction have been performed, such that the actuator 40 has been depressed (demonstrated with 40B), thereby urging the platform distally so as to depress the plunger 90 (shown in FIG. 3C) to the most distal position, followed by retraction of the platform 60 into the actuator lumen 41, shown in FIG. 3D, by way of the single actuation mechanism 150 described in relation to FIGS. 4A-6D.

As can be seen in the implementations of FIGS. 4A-4E, the various collector 10 implementations have a self-locking, or single actuation mechanism 150, meaning a mechanism 150 that prevents repeated use of the collector 10. In these implementations, the actuation mechanism 150 facilitates the actuation and retraction of the internal components, keyed on the translation of linear movement into rotational movement, such that the platform 60 is able to rotate free of the elongate guides 20/actuator arms 44 and retract into the actuator lumen 41 by way of the spring 110 (as best shown in FIG. 3D).

Figure 4A:
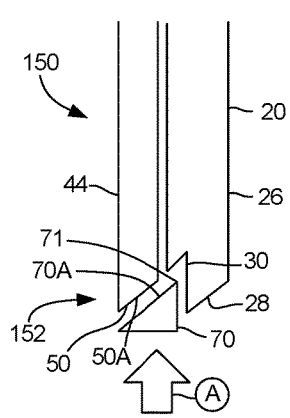
FIG. 4A is a side view of one embodiment of an actuation mechanism.

As shown in the implementations of FIGS. 4A-6D, the mechanism 150 is formed by the substantial alignment of the previously discussed actuator arms 44 of the button 40 and elongate guides 20 the housing 12. In these embodiments, the single actuation mechanism 150 begins in a ready position (prior to being deployed by depressing or otherwise actuating the actuator 40 and actuator arms 44) in relation to the platform projections 60 as is shown in FIGS. 4A and 4D. As will be described in detail below, upon actuation, the single actuation mechanism 150 acts so as translate linear motion into rotational motion and transition to the fired state (where it can no longer be deployed) as is shown in FIGS.

4C and 4E. In this way, the collector 10 is able to provide a single-use, self-locking actuation mechanism 150 and facilitates safe use.

In operation, the self-locking single actuation mechanism 150 is configured to prevent rotational movement of the platform 60. That is, while in the ready position (shown in FIG. 4A, FIG. 5A, FIGS. 6A and 6D), a platform projection 70 is disposed within the projection lock 152, such that the proximal projection end 71 is nested within the projection lock 152 to prevent any lateral movement. In certain embodiments, the projection lock 152 is formed by the alignment of the actuator notch 50 and guide groove 30 when the actuator (shown in FIG. 3A at 40) is in the ready position (as is shown in FIGS. 3 and 4A). As is shown in FIGS. 4A-4E, in these embodiments the actuator notch 50 comprises a substantially planar notch face 50A which is set at an angle complementary to the planar projection face 70A, such that distal movement of the actuator arms 44 will urge the projection 70 laterally. As is described in relation to FIGS. 4F-O, other configurations are possible.

Returning to the embodiments of FIGS. 4A-E, the projection 70 and projection lock 152 are of complementary shapes and configured such that the projection 70 is urged upwards by the force of the spring (the spring is shown in FIG. 2A at 100 and the force is depicted in FIGS. 4A-4E as reference arrow A), so as to be nested or otherwise contained within the projection lock 152. In these implementations, the projection 70 is held in a static position in the projection lock 152 when the actuator is in the ready position: the projection 70 (and correspondingly, the platform 60) is incapable of moving vertically or horizontally (rotationally).

Figure 4B:
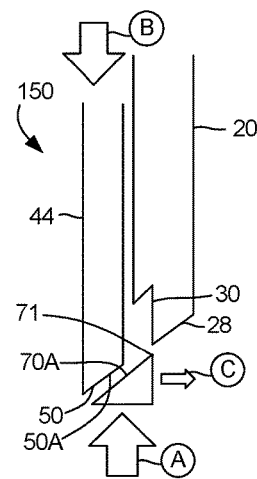
FIG. 4B is a side view of the actuation mechanism embodiment of FIG. 4A, during rotation.

As is shown in FIG. 4B, when the button surface 42 is depressed, the actuation mechanism 150 urges the platform 60, represented by the projection 70, through a distal and rotational actuation path. The actuator arms 44 are urged distally (as is shown by reference arrow B). As shown in the figures, this distal movement disrupts the projection lock 152, as in this embodiment the actuator notch 50 is displaced distally relative to the guide groove 30, thereby imparting both a distal and rotational force on the projection 70 (rotational force shown by reference arrow C) due to the distal movement of the notch 50 past the distal tip of the groove 30. Collectively, the distal movement of reference arrow B and rotational movement of reference arrow C accordingly represent an embodiment of the "actuation path," (which is also shown variously in the figures at 154). As would be apparent to one of skill in the art, the rotational resistance of the platform 60 as well as the spring force can be adjusted to facilitate or prevent the movement of the projection 70 through the actuation path.

Figure 4C:
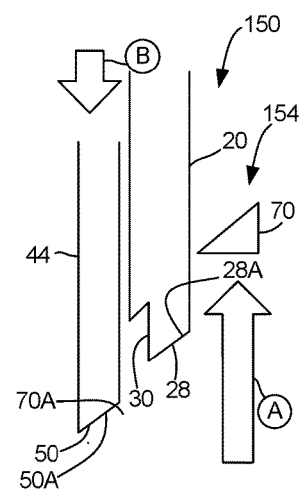
FIG. 4C is a side view of the actuation mechanism embodiment of FIG. 4A, during rotation.
Figure 4D:
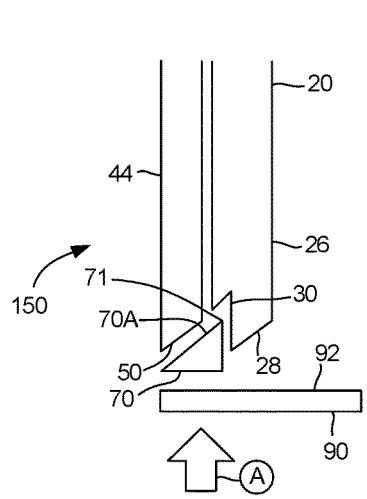
FIG. 4D is a side view of the actuation mechanism embodiment of FIG. 4A, during rotation.

The rotational movement of the projection 70 in the actuation path (also shown in FIGS. 8A-8B) correspondingly moves the platform 60 both distally and rotationally, the distal movement being further imparted onto the plunger 90, as is shown in FIG. 4D, so as deploy the lancets (shown in FIG. 3 at 130) into the surface of a subject's skin. As would be apparent to one of skill in the art, other configurations of the actuator notch 50, guide groove 30 and projection 70 can be utilized in the single actuation mechanism 150.

Figure 4E:
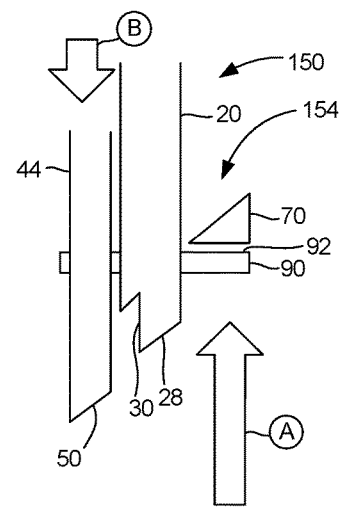
FIG. 4E is a side view of the actuation mechanism embodiment of FIG. 4A, during retraction.

As is shown in FIGS. 4C and 4E, upon sufficient rotational movement of the projection 70, the projection 70 moves out of alignment with the elongate guide 20, so as to next be urged proximally in the retraction path 154. In certain embodiments, the guide notch 28 assists with the rotational and vertical movement, by providing an angled plane 28A (as best shown in FIG. 4C) which assists the projection 70 in so moving. As is shown in FIG. 4E, because the projection 70, and therefore the platform 60, is no longer within the projection lock 152, it is now free to be urged upward by the spring force A past the projection lock 152. In this retraction path 154, the plunger 90 and correspondingly the membrane 80 (on the top plunger surface 92) can extend to a proximal position that is further proximally than their proximal position when in the ready position (as is shown in FIG. 4D, where the projection is within the projection lock 152).

FIGS. 5A-5E depict an alternative embodiment of the actuation mechanism 150. In this embodiment, the actuator arm 44 has an actuator catch 51 and the elongate guide 20 has a guide notch 28 to control the lateral movement of the projection 70 (and correspondingly, the platform, as is shown in FIG. 3A). In these implementations, the actuator catch 51 is disposed at one end of the actuator notch face 50A at a non-zero angle relative to the notch face 50A. Accordingly, the actuator catch 51 comprises a catch face 51A which is configured to impede the proximal progress of the projection 70. Again, in these embodiments the actuator arms 44 and elongate guides 20 can form the projection lock 152. However, in these embodiments the elongate guides 20 can also be disposed to the interior of the device lumen relative to the actuator arms 44 (as is also shown in FIG. 2B).

As is depicted in FIGS. 5A-5E, and as would be appreciated by a skilled artisan, when the actuator arm 44 (shown in FIG. 1A) is depressed, the projection 70 is urged laterally in the direction of the catch 51 and across the catch face 51A, the proximal progress of the proximal projection end 71 is briefly retarded or delayed, thereby causing the projection 70 and platform 60 to "springboard" slightly or otherwise remain in the distal position slightly longer, thus increasing the total time that the plunger (shown in FIG. 10B) is in the distal position. As is discussed below, there are advantages to this enhanced actuation duration.

As shown in FIG. 5A, in the ready position, the single actuation mechanism 150 is again configured to prevent the rotational movement of the platform 60. That is, while in the ready position the platform projection 70 is disposed within the projection lock 152, which is formed by the guide groove 30 and optionally the actuator notch 50. In exemplary embodiments, the projection 70 and projection lock 152 are of complementary shapes and configured such that the projection 70 is urged upwards by the force of the spring (shown as reference arrow A), so as to be nested within the projection lock 152, thereby again holding the projection 70 and platform 60 in a static position.

As is shown in FIG. 5B-5C, when the button surface (shown in FIG. 1B at 42) is depressed, the actuator arms 44 are urged distally in to the firing state, thereby urging the platform 60 and projection 70 through a distal and rotational actuation path (shown at reference arrow C). As shown in FIG. 5C, after the projection 70 has moved laterally, the proximal projection end 71 is brought into contact with the actuator catch 51. Accordingly, the proximal projection end 71 traverses the catch face 51A, thereby delaying the proximal release and retraction of the platform while urging the actuator arm 44 proximally, as designated by reference arrow D. In this embodiment, the proximal projection end 71 continues laterally (reference arrow C) to the distal guide notch end 28B (shown in FIGS. 5C-5D), such that the projection 70 is free to be urged upward by the spring force A past the projection lock 152 in FIG. 5E.

Figure 6A:
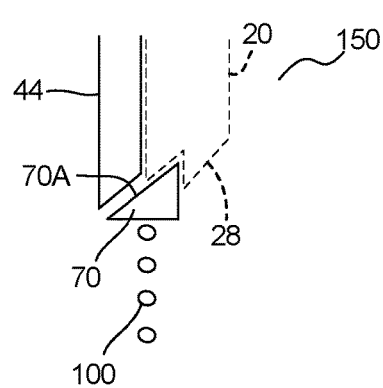
FIG. 6A is a side view of the actuation mechanism comprising a guide notch embodiment.
Figure 6B:
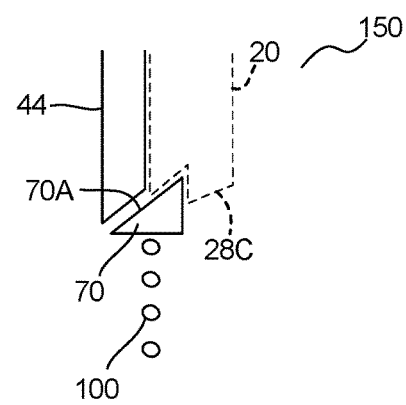
FIG. 6B a further side view of the actuation mechanism comprising another guide notch embodiment.

FIGS. 6A-6D depict various embodiments of the single actuation mechanism 150 comprising a variety of guide notch 28 configurations. FIG. 6A depicts a guide notch 28 which is complementary to the angle of the planar projection face 70A. In FIG. 6B, the guide notch 28C is disposed at an angle which is less than the angle of the projection face 70A angle relative to the surface of the subject's skin (not shown). In this embodiment, the guide notch 28C will induce greater relative downward force than lateral force, thereby slowing the lateral movement of the projection 70 and increasing the time to retraction.

Figure 6C:
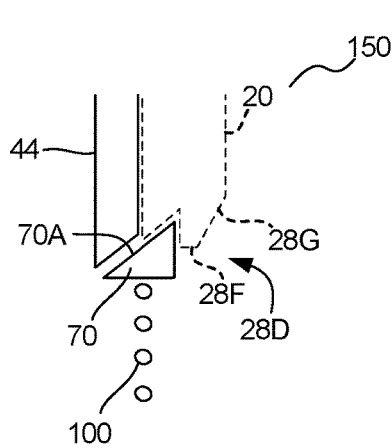
FIG. 6C a further side view of the actuation mechanism comprising another guide notch embodiment.
Figure 6D:
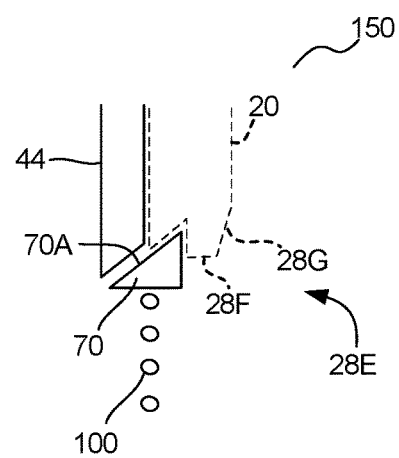
FIG. 6D a further side view of the actuation mechanism comprising yet another guide notch embodiment.

In FIGS. 6C-6D, the guide notches 28D, 28E feature a first guide face 28F and second guide face 28G. In these configurations, the first guide face 28F can be of variable width (as shown by comparing FIG. 6C with FIG. 6D), and the second guide face 28G is angled so as to allow upward projection 70 movement, as has been previously described. In these embodiments, the duration of actuation can thereby be controlled by requiring the proximal projection end 71 to traverse the first guide face 28F laterally prior to freely releasing proximally.

Figure 7:
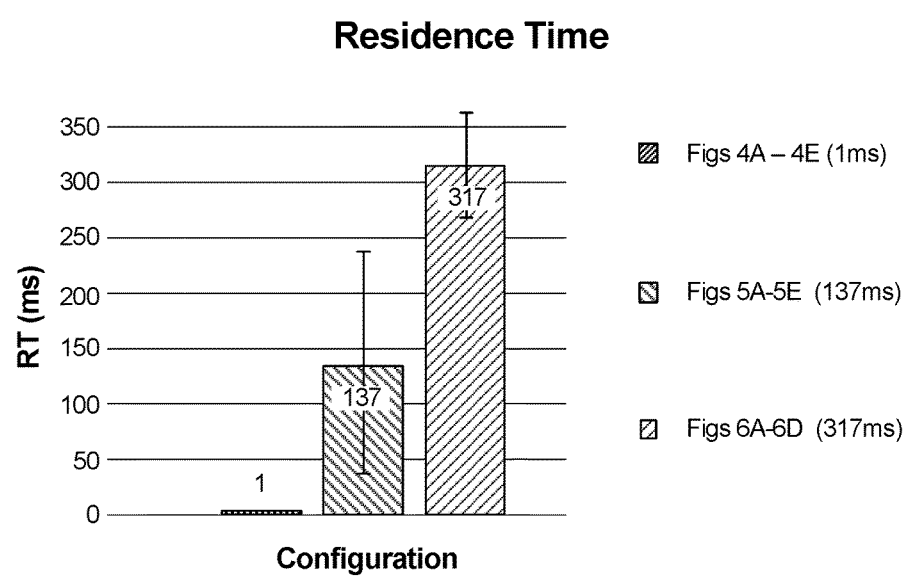
FIG. 7 is a histogram showing average time spent in the distal, fired position according to several embodiments.

FIG. 7 depicts the difference in residence time (in milliseconds) in the actuated state of the embodiments featuring an actuator catch 51 (as shown in FIGS. 5A-5E) as compared with the embodiments without a catch (FIGS. 4A-E) and the embodiments featuring a variable width guide face (FIGS. 6C-6D), that is, while the embodiment in FIGS. 4A-4E has an average residence time of 1 ms, the embodiment of FIGS. 5A-5E has an average residence time of 137 ms and the embodiment of FIGS. 6A-6D has an average residence time of 317 ms.

Figure 8A:
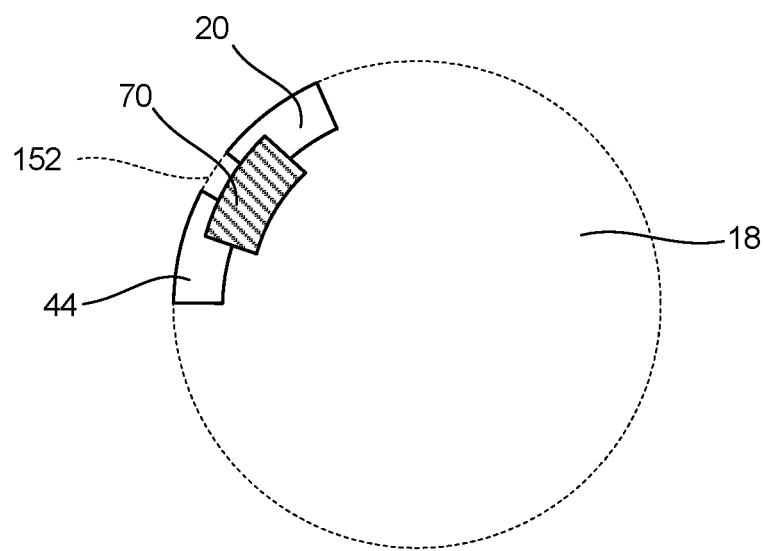
FIG. 8A is a top view schematic of the embodiment of FIG. 1A showing the projection in the projection lock.
Figure 8B:
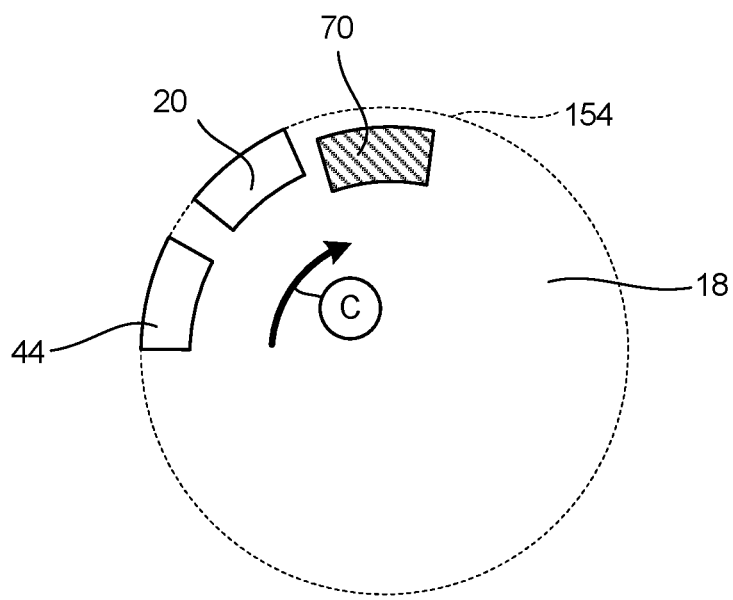
FIG. 8B is a top view schematic of the embodiment of FIG. 1A showing the projection in the retraction position.
Figure 8C:
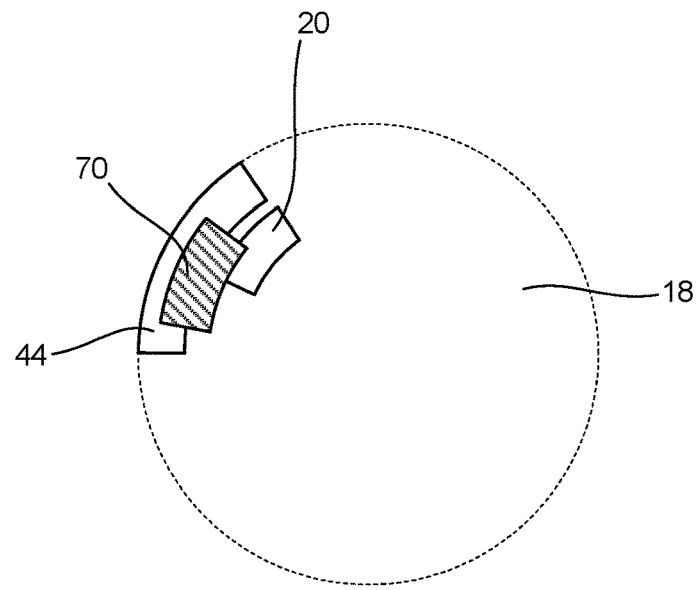
FIG. 8C is a top view schematic of the embodiment of FIG. 2A showing the projection in the projection lock.
Figure 8D:
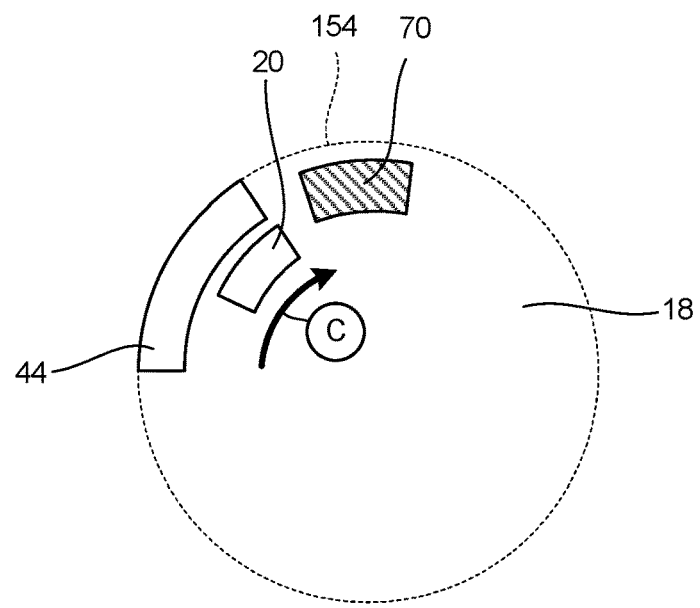
FIG. 8D is a top view schematic of the embodiment of FIG. 2A showing the projection in the retraction position.

As shown in FIGS. 8A-8B, the actuator arms 44 and elongate guides 20 are disposed adjacently within the lumen 18 in the embodiments of FIGS. 1A, 2A and 4A-E, both being positioned along the inner wall of the lumen 18. However, as shown in FIGS. 8C-8D, in the embodiments of FIGS. 1B, 2B and 4F-J, the elongate guides 20 can be disposed centrally in the lumen relative to the actuator arms 44 (that is, the elongate guides 20 can be disposed further away from the inner wall of the lumen 18 and closer to the center thereof).

Turning to the post-actuation retraction of these components, the proximal movement of the plunger and membrane can be utilized to create a vacuum within the collector 10 so as to facilitate fluid collection. FIGS. 9A-10C depict further views of the actuator 40 and housing 12, as well as the membrane 80 and plunger 90. In exemplary embodiments, the membrane 80 is a unified membrane body 80 comprised of a single piece of a flexible material, such as silicone, rubber, thermoplastic elastomer ("TPE"), thermoplastic vulcanizate ("TPV"), or thermoplastic polyurethane ("TPU"), so as to be capable of flexible movement in response to the movement of the platform 60 and plunger 90, as is described below in relation to FIGS. 10A-10C.

As is also shown in FIGS. 9A-15B, in exemplary embodiments of the collector 10, the membrane 80 forms a fluidic and hermetic seal 87 within the membrane lumen 86 (as best shown in FIGS. 10A-10D and 13B) around the plunger 90, collection apertures 132, base 110, distal surface 120 and any network 116 of fluidic channels or passages for transporting collected fluid to the collection tube 34 which may be contained therein. These implementations can incorporate any of the previously described methods, devices and systems, such as those for fluid collection, transport and storage in the incorporated references, including all disclosures in U.S. Pat. No. 9,289,763, U.S. application Ser. No. 14/932,485, U.S. application Ser. No. 13/750,526, and U.S. application Ser. No. 14/816,994.

In these embodiments of FIGS. 9A-15B, the plunger 90 further comprises a central valve opening 95. The central valve opening 95 is configured to allow the passage of gases through the plunger coupling 96 into the membrane lumen 86 as part of the one-way valve 160 described below.

Figure 10A:
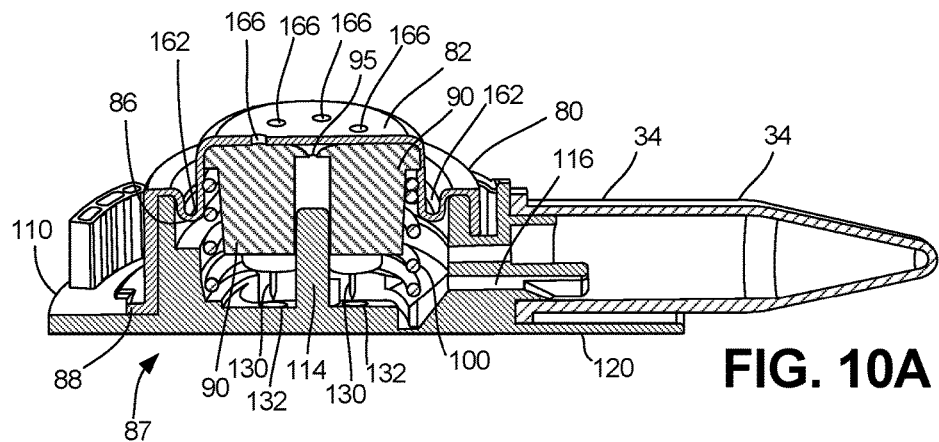
FIG. 10A is a perspective cutaway cross-sectional view of the plunger and membrane within the collector in the ready position, according to an exemplary embodiment.
Figure 10B:
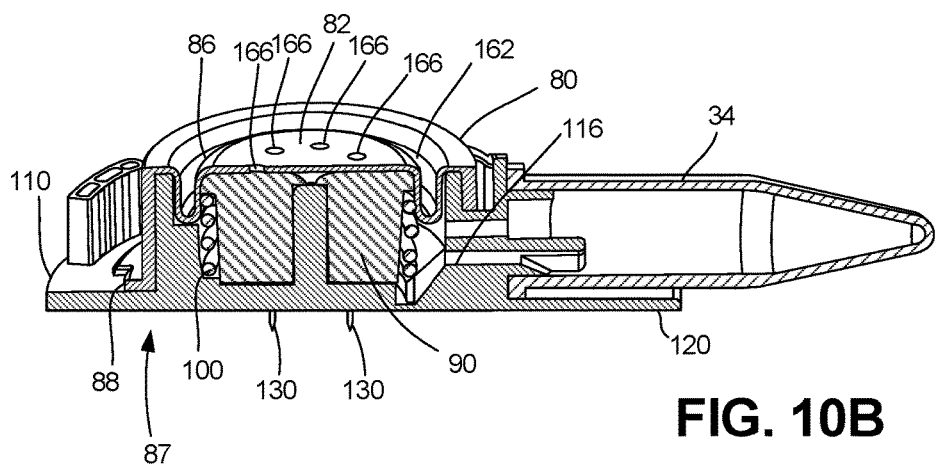
FIG. 10B is a perspective cutaway cross-sectional view of the plunger and membrane within the collector in the actuated position, according to an exemplary embodiment.
Figure 10C:
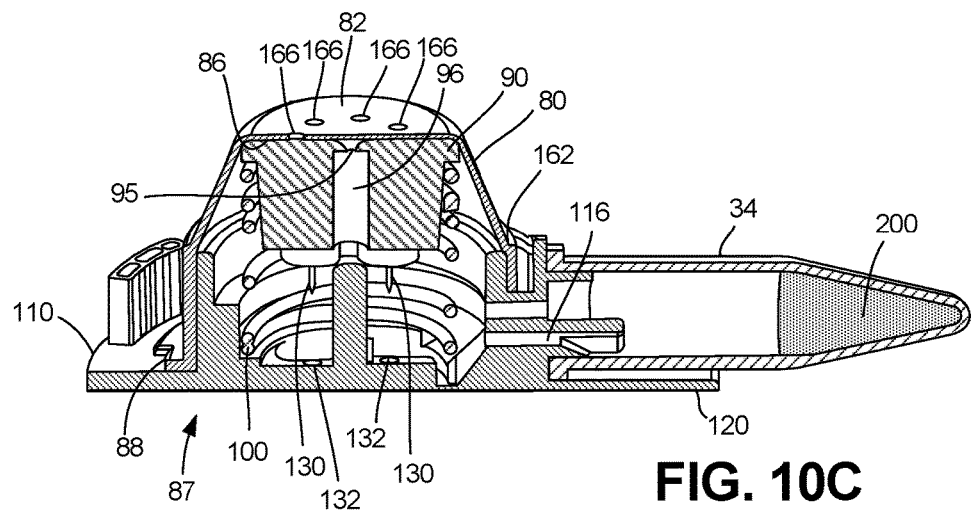
FIG. 10C is a perspective cutaway cross-sectional view of the plunger and membrane within the collector in the retracted position, according to an exemplary embodiment.

As shown in FIG. 10A, the collector 10 is in the "ready" position. In FIG. 10B, the collector 10 has been actuated by a user depressing the actuator 40 such that the plunger 90 is in the most distal position as a result. Movement of the plunger 90 to the distal position causes the lancets 130 to extend past the distal surface 120 of the base 110 (as best shown in FIG. 10B) by way of the collection apertures 132. Through the actuation of the collector 10, the lancets 130 are able to pierce the skin of a subject and initiate the flow of fluid 200 into the collection apertures 132, the passages or network 116 and eventually into the collection tube 34 as has been previously described, for example in relation to U.S. application Ser. No. 14/816,994, which has been incorporated by reference in its entirety. The collection position is also shown in FIG. 10C, wherein the plunger 90 has been extended proximally past the ready position through the retraction path, and fluid 200 has been collected in the collection tube 34.

As discussed above and as shown in FIGS. 10A-20C, the creation of a vacuum within the membrane lumen 86 can help to facilitate fluid flow. In certain embodiments, the membrane 80 further comprises a outlet channel 32 (best shown in FIG. 9B) which is configured to be in fluidic and hermetic communication with a collection tube (shown for example in FIGS. 1A-B at 34) or another collection system, as has been previously described, for example in relation to U.S. application Ser. No. 14/816,994. In various implementations, a circular membrane lip 88 is provided to be fixedly attached to the base 110 and create the hermetic and fluidic seal 87. In exemplary embodiments, the membrane lumen 86 can be kept sterile as a result of the seal 87, while the remaining aspects of the central lumen need not be.

Figure 9A:
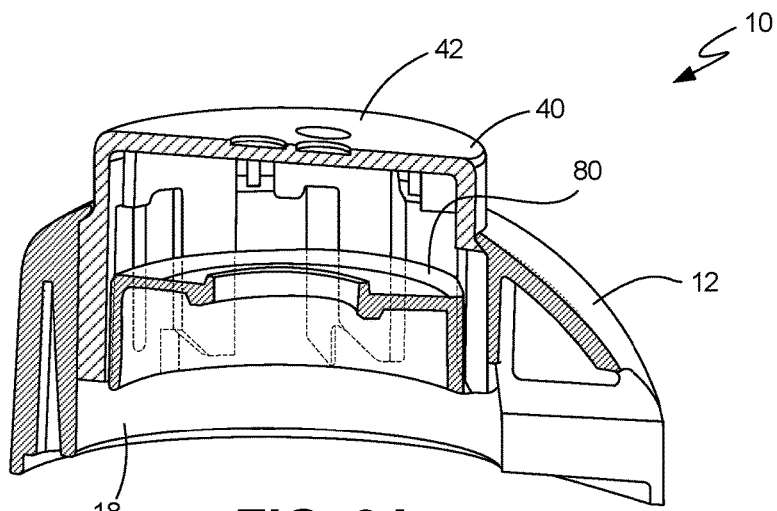
FIG. 9A is a perspective cross-sectional view of the button, housing and membrane, according to an exemplary embodiment.
Figure 9B:
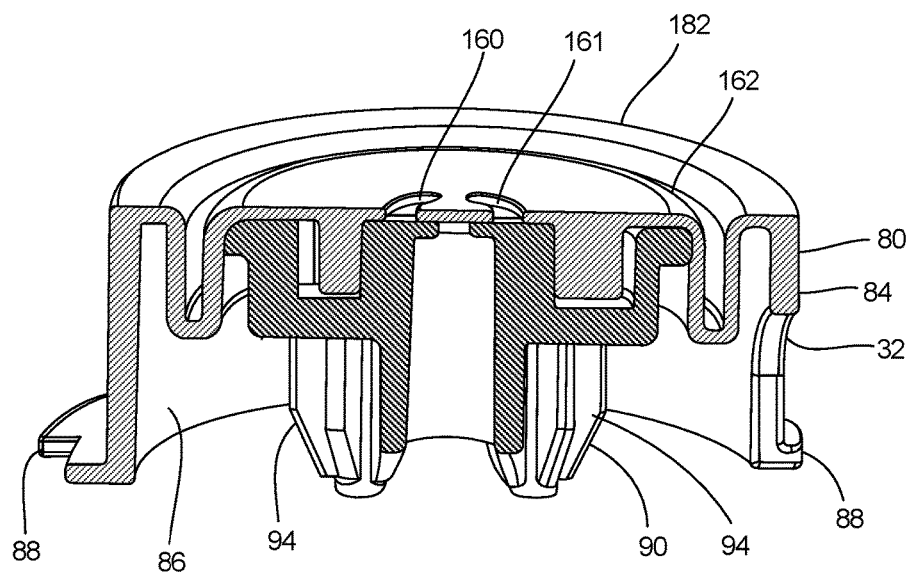
FIG. 9B is a perspective cross-sectional view of the membrane and plunger, according to an exemplary embodiment.

Importantly, because the membrane 80 is flexible and can be deformed and thereby cause the interior volume of the membrane lumen 86 to change, this volume change can alter the pressure inside the fluidic and hermetic seal 87 of the lumen 86. In exemplary embodiments as best shown in FIG. 9B, the membrane 80 further comprises a one-way valve 160 configured to allow the air contained within the membrane lumen 86 to escape in response to the downward motion of the platform 60. In some implementations, this one-way valve 160 can be made up of at least one slit 161. As shown in FIGS. 10A-11C, in various embodiments, the one-way valve 160 can have one or more one-way valve openings 166 or slits 161 disposed about the top membrane surface 82 in a variety of configurations, such as those shown in FIGS. 11A-C. Other embodiments are possible, as would be apparent to one of skill in the art.

Returning to FIG. 10B, in response to actuation, the plunger 90 is urged distally, and the membrane 80 is compressed. However, the pressure inside the membrane lumen 86 stays at substantially atmospheric pressure as air within the membrane lumen 86 is urged out of the central valve opening 95 and through the slits 161 or openings 166 of the one-way valve 160. The central lumen (shown in FIGS. 2A-2B at 18) also continues to be at or near atmospheric pressure when it is deformed distally by this movement, as there is no such seal around the platform 60, or between the actuator 40 and housing 12. At substantially the same time, the lancets 130 puncture the skin of the subject, thereby inducing fluid collection from the subject's skin.

Following the completion of the actuation process, and as shown in FIG. 10C, the plunger 90 is urged proximally through the retraction path by way of spring 100, as described above in relation to FIGS. 4C and 4E. This upward, proximal movement of the plunger 90 causes a corresponding movement of the top membrane surface 82 away from the circular membrane lip 88 and distal surface 120 of the base 110 (shown in FIGS. 1A-B). This movement results in an expansion of the membrane lumen 86 volume. The one-way valve 160 (which could be slits 161 or one-way valve openings 166 disposed in a variety of configurations, as shown in FIGS. 11A-C) prevents air from entering the membrane lumen 86. The resulting pressure drop within the membrane lumen 86 creates a vacuum relative to atmospheric pressure, thereby encouraging fluid flow from the subject into the collection apertures 132. Again, this is because the one-way valve 160 is configured such that it does not allow air to enter the membrane lumen 86. As such, the post-actuation retraction can create a vacuum which facilitates fluid collection.

Certain embodiments of the top membrane surface 82 have bellows 162, which facilitate the movement of the membrane 80 and the increase in volume of the membrane lumen 86, as is shown in FIGS. 10A-10C. In these embodiments, the bellows 162 can allow the membrane 80 to easily move between the various positions without unnecessary stretching of the membrane 80. This allows for air to be more efficiently moved out of the membrane lumen 86, and can guide the plunger 90 distally and proximally through the actuation and retraction paths, respectively. Accordingly, this movement of the bellows 162 can be achieved without impeding the operational path of the plunger 90 as it moves along the cylindrical membrane wall 84.

As shown in FIGS. 11A-11C, various one-way valve 160 configurations featuring one or more slits 161 or openings 166 are possible, respectively. FIG. 11D demonstrates that each of these various membrane 80 configurations can result in variations in the vacuum pressure generated in kPa.

Figure 11E:
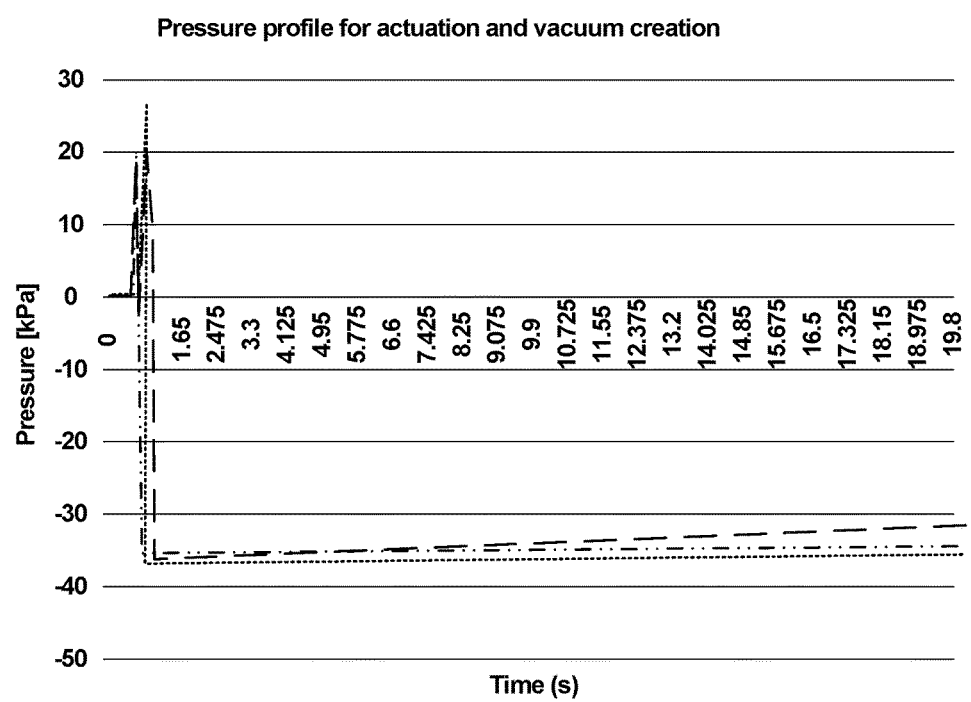
FIG. 11E is a chart of the pressure profile for actuation and vacuum creation over the course of actuation and retraction, according to an exemplary embodiment.

The pressure profile for actuation and vacuum creation is shown in FIG. 11E. In this example, the pressure inside the membrane 80 was assessed during actuation and retraction of the device over time in kPa. The results demonstrate the initial increase in pressure inside the device, which is followed by an extended period of vacuum pressure which remains relatively constant, but in certain embodiments can decay slightly over the course of the 20 seconds shown. As would be apparent to one of skill in the art, and as previously discussed, the creation of this vacuum within the device facilitates blood draw.

Figure 12A:
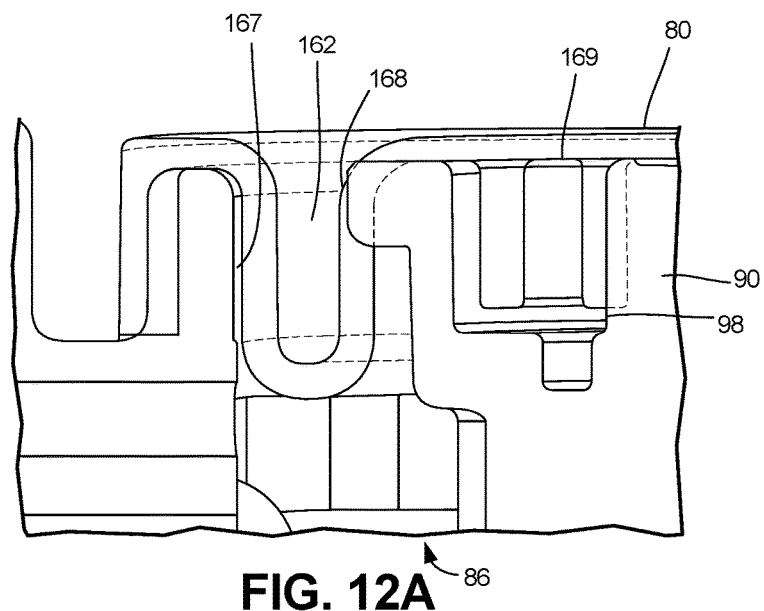
FIG. 12A is a close-up cross-sectional view of the bellows, according to an exemplary embodiment.

In the embodiment of FIG. 12A, the bellows 162 utilize a rolling membrane design. This design is a U-shaped membrane (shown at 162) that allows the bellows 162 to roll along the outer wall 167 and inner wall 168 during actuation (as shown in FIGS. 10A-10C). In exemplary embodiments, the bellows are configured to elongate during retraction to allow a vacuum to be created inside the membrane lumen 86. Stiffer materials, such as those which exceed Shore 30A can be effective during the air expulsion process. As is also shown in FIG. 12A, in certain embodiments the plunger 90 comprises a membrane opening 98, which is configured to secure a membrane component member 169. In these implementations, the member 169 is a portion of the membrane that is fitted into the opening in the manner of a plug, so as to provide enhanced membrane 80 and bellows 162 stability and to facilitate the creation of a proper seal within the membrane lumen 86.

Figure 12B:
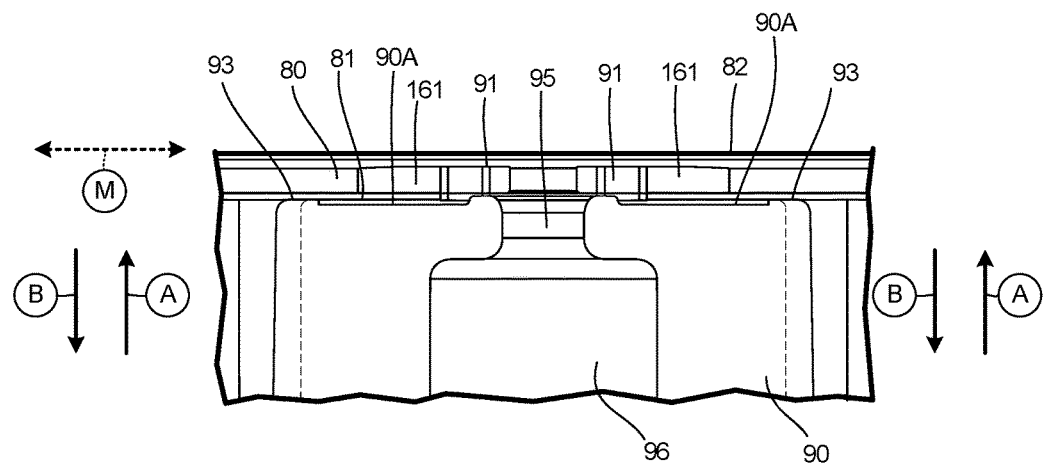
FIG. 12B is a close-up cross-sectional view of the membrane and plunger, according to an exemplary embodiment comprising ridges.

In various alternate embodiments, and that of FIG. 12B, the connection between the membrane 80 and plunger 90 can comprise at least one ridge on the plunger's proximal face 90A. In this embodiment, the plunger 90 has an inner ridge 91 which is adjacent to the central valve opening 95 and an outer ridge 93 which is adjacent to the bellows 162. In these embodiments, the inner ridge 91 can facilitate the creation of a seal between the membrane 80 and plunger 90 to facilitate the opening and closing of the valve slit 161 or opening 166.

As shown in FIG. 12B, the outer ridge 93 can prevent tenting by reducing or eliminating the development of tension between the membrane 80 and the inner ridge 91 (designated in FIG. 12B as the membrane portion 81). During actuation, the platform 60 is urged distally (shown at reference arrow B) and then, during retraction, proximally by the force of the spring (shown as reference arrow A). During actuation and retraction, tension can develop in the membrane portion 81, and this tension can limit the ability of the membrane 80 to release air during the actuation process (described above in relation to FIGS. 9A-11E).

Accordingly, as shown in FIG. 12B, the outer ridge 93 is configured to align the portion of the membrane 80 between the inner ridge 91 and outer ridge into a plane (shown by reference line M) which is substantially perpendicular from the direction of actuation (shown by reference arrows A and B), thereby preventing tenting about the inner ridge 91.

Figure 13A:
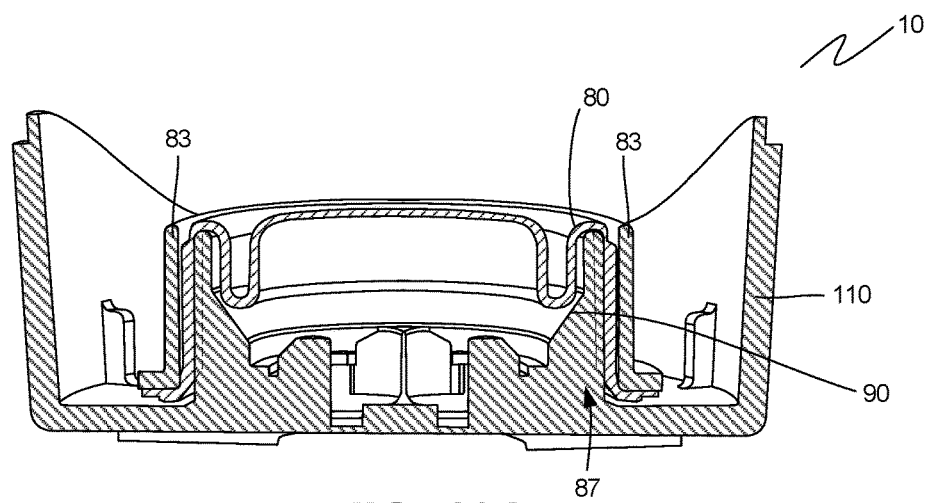

In the implementation of FIG. 13A, the base 110 further comprises a membrane collar 83 fitted around the membrane 80. In these implementations, the relatively rigid membrane collar 83 serves to compress or otherwise secure the flexible membrane 80 around the plunger 90.

It is understood that the membrane collar 83 can be effective in maintaining the membrane seal 87 and preventing the expulsion of air from the membrane other than through the one-way valve. In these implementations, the membrane collar 83 also prevents the "rubbing" of the platform 60 on the membrane 80.

Figure 13B:
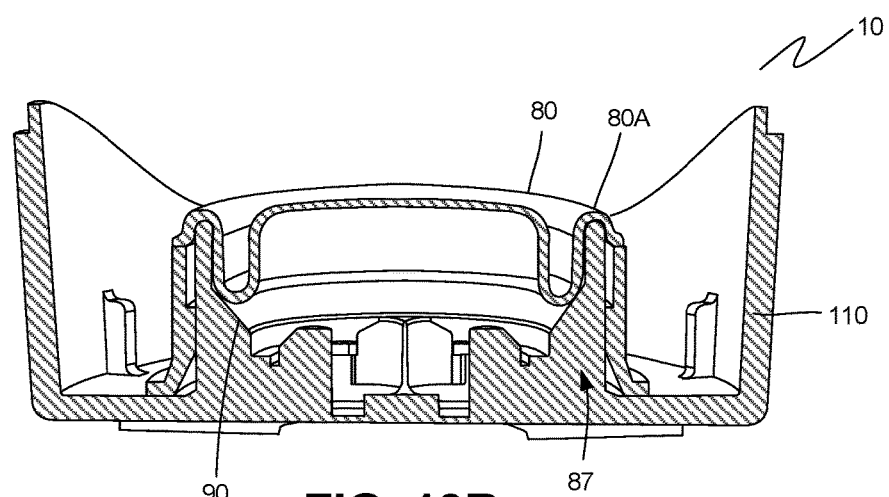

In FIG. 13B, a membrane 80 having an operationally integrated overmold 89 is shown. In these implementations, the top, flexible portion comprises an elastomer membrane 89A, which extends distally around the plunger, where it is integrated with an a rigid lower flange 89B. In various implementations, the lower flange 89B is polypropylene, or some other similar material.

Figure 14A:
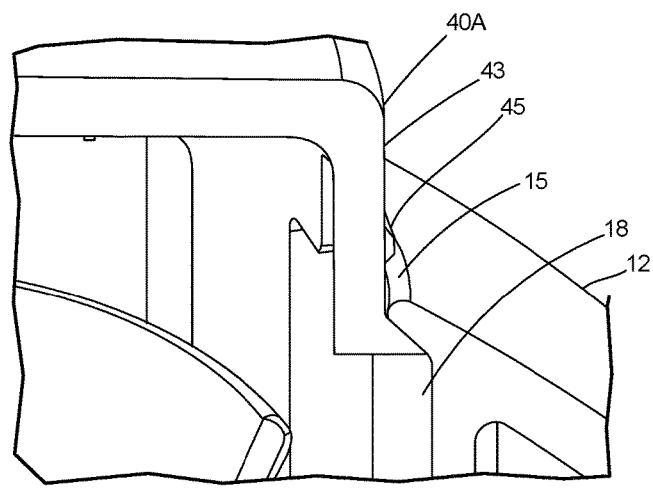
FIG. 14A is a close-up perspective cut-away view of a threshold stop, according to an exemplary embodiment.
Figure 14B:
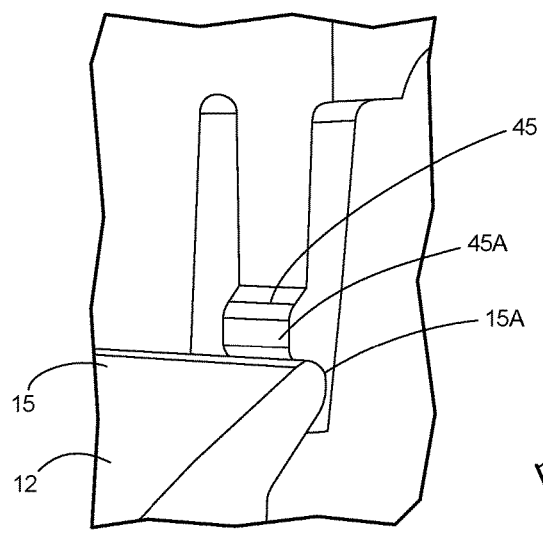
FIG. 14B is a further close-up, three-quarters perspective cut-away view of a threshold stop, according to an exemplary embodiment.
Figure 14C:
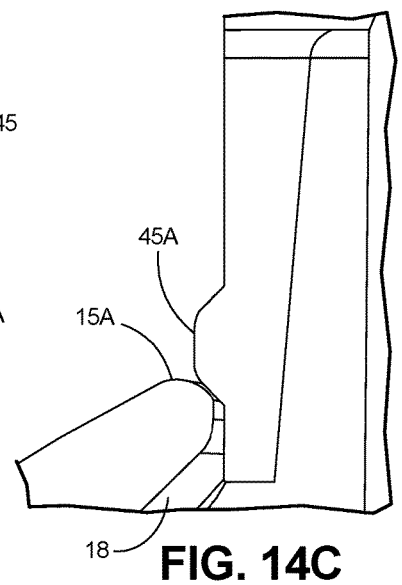
FIG. 14C is a further close-up, side cut-away view of a threshold stop, according to an exemplary embodiment.

As is shown in FIGS. 14A-14C, in certain embodiments, the actuator 40 has a threshold stop 45. In exemplary embodiments, the threshold stop 45 is a protrusion 45A disposed on the button wall 43. Prior to use, the actuator's button 40A is positioned above the proximal end 14 of the housing 12 in the "ready" position, the button wall 43 further being substantially aligned with the lumen lip 15 of the housing, which is described above. As is shown in FIGS. 14A-14C, the protrusion 45A is disposed so as to abut against the lumen lip 15 on the top side 15A.

In the embodiments of FIGS. 14A-14C, the threshold stop 45 and/or lumen lip 15 can be comprised of deformable materials, such as thermoplastics (such as polypropylene, polyethylene, or acrylonitrile butadiene styrene ("ABS"), or TPEs, so as to physically prevent the distal movement of the actuator 40 unless a force sufficient to deform the threshold stop 45 and/or lumen lip 15 is applied. This threshold force requirement thereby holds the actuator 40 in the "ready" position absent the application of sufficient downward, or distal, force to the button 40A. In alternative embodiments, the threshold stop 45 can be made of materials known in the art to fracture in response to a threshold force.

Figure 15A:
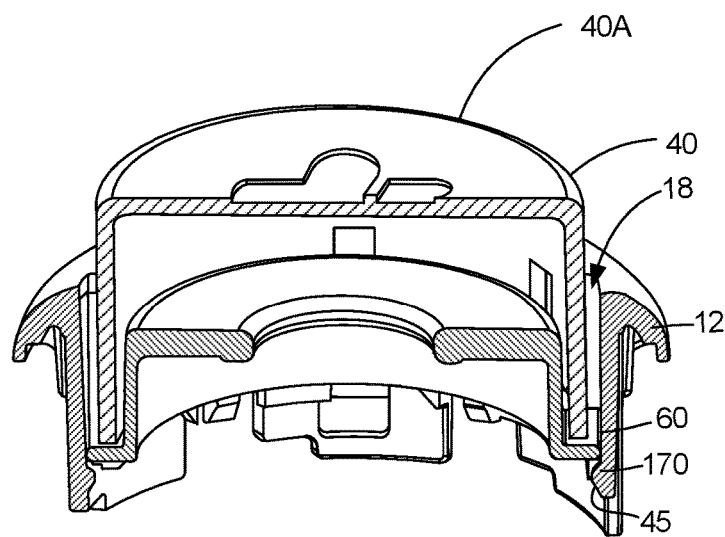
FIG. 15A is a close-up perspective cut-away view of a threshold stop, according to another exemplary embodiment.
Figure 15B:
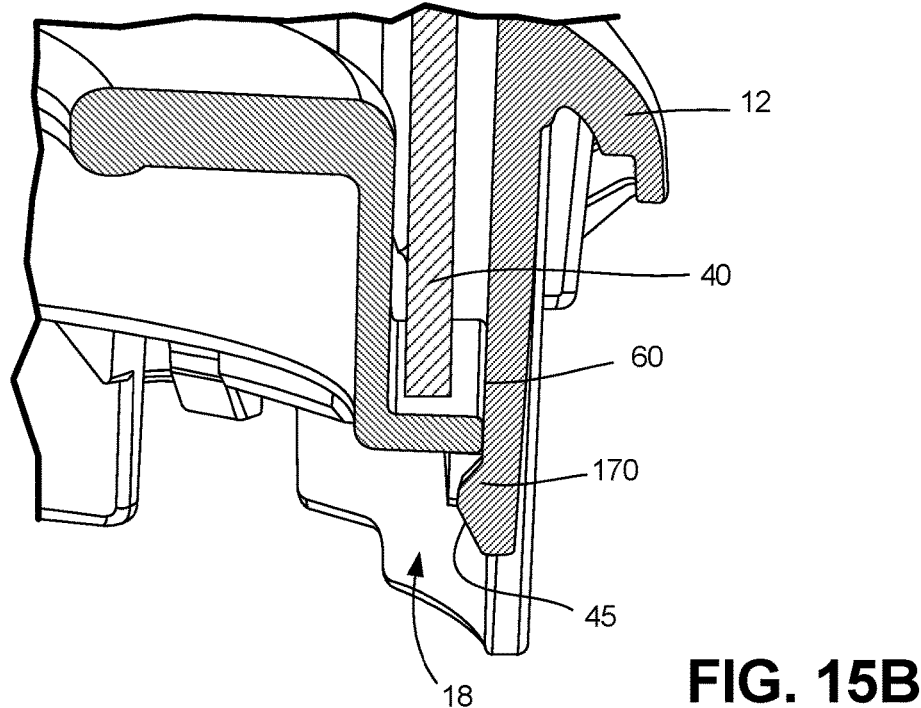
FIG. 15B is a further close-up, three-quarters perspective cut-away view of the implementation of FIG. 15A.

In various alternate implementations, and as shown in FIGS. 15A-15B, the threshold stop 45 is disposed at the end of at least one elongate, cantelevered arm 170. Unlike the implementations of FIGS. 14A-140, the cantelevered arm 170 in these implementations are disposed inside the lumen 18, further away from the cover 12 as opposed to on the surface of the button 40, as shown in FIGS. 14A-14C. In this implementation, the threshold stops 45 are in operational communication with the platform 60, as opposed to the button 40, thereby keeping the whole subassembly together as a subunit, further simplifying the assembly process by allowing the unit to remain static during movement in the assembly process. It is understood that this configuration allows for larger threshold stops 45 and higher or lower tolerances in press force.

Because a sufficient force is required to cause actuation in these embodiments, the collector 10 can both prevent accidental actuation and ensure that the actuation force applied is sufficient to break the skin of the subject and result in a fluid draw. Further, because the actuation path is independent from the retraction path (as described above in relation to FIGS. 4A-4E), the internal components of the collector 10 can be brought to a position that cannot be re-actuated, thereby preventing subsequent use.

Further, the collector 10 allows for the ability to control the amount of force, and correspondingly the velocity, required for actuation. This is because the threshold stop 45 and the actuation mechanism 150 can be controlled by way of the platform 60 rotation and spring resistance described above in relation to FIGS. 4A-4E. The control allows for the precise determination of lancet 130, or needle penetration into a subject's skin. This is because the engineered lancet throw distance can impact the volume and type of bodily fluid extracted from the tissue, in particular ratio of blood to interstitial fluid which is drawn. In certain embodiments, this engineered distance can be between 1 mm and 5 mm.

Although the disclosure has been described with reference to preferred embodiments, persons skilled in the art will recognize that changes may be made in form and detail without departing from the spirit and scope of the disclosed apparatus, systems and methods.

What is claimed is:

1. A collector for collecting fluid from a subject, the collector comprising:
    a housing having a base and an elongate guide, wherein the housing defines a lumen, and wherein a distal surface of the base is configured to be positioned against a skin surface of the subject;
    an actuator positioned at least partially within the lumen and having an actuator arm, wherein a distal portion of the elongate guide and a distal portion of the actuator arm together define a locking feature, and wherein the actuator is configured to be moved through the lumen toward the base;
    a platform positioned at least partially within the lumen between the actuator and the base, wherein the platform includes a platform projection configured to engage the locking feature;
    and
    a plunger operably coupled to the platform and having a lancet,
        wherein the actuator is movable from (a) a first position relative to the base in which the lancet extends past the distal surface of the base and (b) a second position nearer to the base than the first position in which the lancet is withdrawn into the lumen of the housing, and
        wherein movement of the actuator from the first position to the second position moves the platform projection out of engagement with the locking feature to permit the platform to move through the lumen relative to the actuator in a direction away from the base.

2. The collector of claim 1, further comprising a membrane disposed within the lumen, wherein the membrane is configured to create a fluidic seal within the lumen.

3. The collector of claim 2, wherein the membrane comprises a membrane lumen and a one way valve configured to create a vacuum within the membrane lumen.

4. The collector of claim 2, wherein the membrane comprises a bellows.

5. The collector of claim 1 wherein the distal portion of the actuator arm includes a distal face and a catch face extending from the distal face at a non-zero angle relative to the distal face.

6. The collector of claim 5 wherein the platform projection engages the catch face in the first position.

7. The collector of claim 5 wherein the platform projection is configured to move along the distal face when the actuator is moved toward the base, and wherein the catch face is configured to delay the platform projection from moving out of engagement with the locking feature to increase the total time the lancet extends past the distal surface of the base.

8. The collector of claim 1 wherein movement of the actuator toward the base rotates the platform relative to the base.

9. The collector of claim 1 wherein the actuator engages the platform when the actuator is in the first position, and wherein the actuator does not engage the platform when the actuator is in the second position.

10. The collector of claim 1, further comprising a spring operably coupling the platform to the base, wherein the spring is configured to drive the platform in the direction away from the base when the actuator is moved to the second position and the platform projection disengages the locking feature.

11. The collector of claim 1 wherein the elongate guide is positioned further toward the interior of the lumen than the actuator arm.

* * * * *

UNITED STATES PATENT AND TRADEMARK OFFICE
CERTIFICATE OF CORRECTION

PATENT NO. : 10,426,390 B2
APPLICATION NO. : 15/387177
DATED : October 1, 2019
INVENTOR(S) : Erwin Berthier et al.

Page 1 of 1

It is certified that error appears in the above-identified patent and that said Letters Patent is hereby corrected as shown below:

In the Specification

Column 1, Lines 17–19, under "FEDERALLY SPONSORED RESEARCH OR DEVELOPMENT," with the following paragraph:
-- This invention was made with government support under Award # 1 R44 DK108689-01 from the Department of Health and Human Services of National Institutes of Health (NIH). The government has certain rights in the invention. --

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*